US00RE43316E

(19) United States
(12) Reissued Patent
Brown et al.

(10) Patent Number: US RE43,316 E
(45) Date of Reissued Patent: Apr. 17, 2012

(54) DIABETES MANAGEMENT SYSTEM AND METHOD FOR CONTROLLING BLOOD GLUCOSE

(75) Inventors: Stephen J. Brown, Woodside, CA (US); David L. Worthington, La Honda, CA (US)

(73) Assignee: Health Hero Network, Inc., Palo Alto, CA (US)

(21) Appl. No.: 10/950,226

(22) Filed: Sep. 23, 2004

Related U.S. Patent Documents

Reissue of:
(64) Patent No.: 6,379,301
Issued: Apr. 30, 2002
Appl. No.: 09/163,807
Filed: Sep. 30, 1998

U.S. Applications:
(63) Continuation-in-part of application No. 08/844,245, filed on Apr. 18, 1997, now Pat. No. 5,822,715, which is a continuation-in-part of application No. 08/781,278, filed on Jan. 10, 1997, now Pat. No. 5,956,501.

(51) Int. Cl.
*A61B 5/05* (2006.01)
*A61B 10/00* (2006.01)
*A61N 2/00* (2006.01)
*G06F 17/00* (2006.01)

(52) U.S. Cl. ..... 600/309; 600/300; 600/365; 128/920; 705/3; 702/19

(58) Field of Classification Search ..... 600/309, 600/365

See application file for complete search history.

(56) References Cited

U.S. PATENT DOCUMENTS 3,426,150 A 2/1969 Tygart
3,566,365 A 2/1971 Rawson et al.
3,566,370 A 2/1971 Worthington, Jr. et al.
(Continued)

FOREIGN PATENT DOCUMENTS

EP 0251520 7/1988
(Continued)

OTHER PUBLICATIONS

"Blood Glucose Monitors", *Portable Health Device,* (1988),vol. 17(9), pp. 253-271.

(Continued)

*Primary Examiner* — Patricia Mallari
*Assistant Examiner* — Karen E Toth
(74) *Attorney, Agent, or Firm* — Christopher P. Maiorana, PC

(57) ABSTRACT

A diabetes management system for predicting a future blood glucose value of a patient and for recommending a corrective action to the patient when the future blood glucose value lies outside of a target range. The system includes a patient-operated apparatus for measuring blood glucose values and for storing data relating to insulin doses administered to the patient. The apparatus predicts the patient's future blood glucose value based upon the patient's current blood glucose value, the fraction of insulin action remaining from the insulin doses, and the patient's insulin sensitivity. The apparatus also determines the corrective action for the patient when the predicted blood glucose value lies outside of a target range. The system also includes a physician computer in communication with the apparatus for receiving the blood glucose values and insulin dose data and for calculating an adjusted insulin sensitivity for use in subsequent predictions.

50 Claims, 9 Drawing Sheets

U.S. PATENT DOCUMENTS

| | | | |
|---|---|---|---|
| 3,768,014 | A | 10/1973 | Smith |
| 3,910,257 | A | 10/1975 | Fletcher et al. |
| 3,920,005 | A | 11/1975 | Gombrich et al. |
| 3,996,928 | A | 12/1976 | Marx |
| 4,004,577 | A | 1/1977 | Sarnoff |
| 4,130,881 | A | 12/1978 | Haessler et al. |
| 4,150,284 | A | 4/1979 | Trenkler et al. |
| 4,151,407 | A | 4/1979 | McBride et al. |
| 4,151,831 | A | 5/1979 | Lester |
| 4,173,971 | A | 11/1979 | Karz |
| 4,216,462 | A | 8/1980 | McGrath et al. |
| 4,227,526 | A | 10/1980 | Goss |
| 4,253,521 | A | 3/1981 | Savage |
| 4,259,548 | A | 3/1981 | Fahey et al. |
| 4,270,547 | A | 6/1981 | Steffen et al. |
| 4,296,756 | A | 10/1981 | Dunning et al. |
| 4,347,568 | A | 8/1982 | Giguere et al. |
| 4,347,851 | A | 9/1982 | Jundanian |
| 4,360,345 | A | 11/1982 | Hon |
| 4,417,306 | A | 11/1983 | Citron et al. |
| 4,422,081 | A | 12/1983 | Woods et al. |
| 4,449,536 | A | 5/1984 | Weaver |
| 4,465,077 | A | 8/1984 | Schneider |
| 4,473,884 | A | 9/1984 | Behl |
| 4,519,398 | A | 5/1985 | Lisiecki et al. |
| 4,531,527 | A | 7/1985 | Reinhold, Jr. |
| 4,546,436 | A | 10/1985 | Schneider et al. |
| 4,566,461 | A | 1/1986 | Lubell et al. |
| 4,576,578 | A | 3/1986 | Parker et al. |
| 4,592,546 | A | 6/1986 | Fascenda et al. |
| 4,627,445 | A | 12/1986 | Garcia |
| 4,674,652 | A | 6/1987 | Aten et al. |
| 4,686,624 | A | 8/1987 | Blum et al. |
| 4,694,490 | A | 9/1987 | Harvey et al. |
| 4,695,954 | A | 9/1987 | Rose et al. |
| 4,712,562 | A | 12/1987 | Ohayon et al. |
| 4,722,349 | A | 2/1988 | Baumberg |
| 4,729,381 | A | 3/1988 | Harada et al. |
| 4,731,726 | A | 3/1988 | Allen, III |
| 4,768,229 | A | 8/1988 | Benjamin et al. |
| 4,779,199 | A | 10/1988 | Yoneda et al. |
| 4,782,511 | A | 11/1988 | Nemec et al. |
| 4,796,639 | A | 1/1989 | Snow et al. |
| 4,799,199 | A | 1/1989 | Scales, III et al. |
| 4,803,625 | A | 2/1989 | Fu et al. |
| 4,835,372 | A | 5/1989 | Gombrich et al. |
| 4,838,275 | A | 6/1989 | Lee |
| 4,858,354 | A | 8/1989 | Gettler |
| 4,858,617 | A | 8/1989 | Sanders |
| 4,890,621 | A | 1/1990 | Hakky |
| 4,897,869 | A | 1/1990 | Takahashi |
| 4,907,973 | A | 3/1990 | Hon |
| 4,933,873 | A | 6/1990 | Kaufman et al. |
| 4,950,246 | A | 8/1990 | Muller |
| 4,953,552 | A | 9/1990 | DeMarzo |
| 4,958,632 | A | 9/1990 | Duggan |
| 4,958,641 | A | 9/1990 | Digby et al. |
| 4,967,756 | A | 11/1990 | Hewitt |
| 4,977,899 | A | 12/1990 | Digby et al. |
| 4,979,509 | A | 12/1990 | Hakky |
| 5,007,429 | A | 4/1991 | Treatch et al. |
| 5,016,172 | A | 5/1991 | Dessertine |
| 5,019,974 | A | 5/1991 | Beckers |
| 5,024,225 | A | 6/1991 | Fang |
| 5,025,374 | A | 6/1991 | Roizen et al. |
| 5,034,807 | A | 7/1991 | Von Kohorn |
| 5,036,462 | A | 7/1991 | Kaufman et al. |
| 5,049,487 | A | 9/1991 | Phillips et al. |
| 5,050,612 | A | 9/1991 | Matsumura |
| 5,056,059 | A | 10/1991 | Tivig et al. |
| 5,059,394 | A | 10/1991 | Phillips et al. |
| 5,065,315 | A | 11/1991 | Garcia |
| 5,068,536 | A | 11/1991 | Rosenthal |
| 5,074,317 | A | 12/1991 | Bondell et al. |
| 5,077,476 | A | 12/1991 | Rosenthal |
| 5,095,798 | A | 3/1992 | Okada et al. |
| 5,109,414 | A | 4/1992 | Harvey et al. |
| 5,109,974 | A | 5/1992 | Beer et al. |
| 5,111,396 | A | 5/1992 | Mills et al. |
| 5,111,817 | A | 5/1992 | Clark et al. |
| 5,111,818 | A | 5/1992 | Suzuki et al. |
| 5,120,230 | A | 6/1992 | Clark et al. |
| 5,120,421 | A | 6/1992 | Glass et al. |
| 5,128,752 | A | 7/1992 | Von Kohorn |
| 5,134,391 | A | 7/1992 | Okada |
| 5,142,358 | A | 8/1992 | Jason |
| 5,142,484 | A | 8/1992 | Kaufman et al. |
| 5,176,502 | A | 1/1993 | Sanderson et al. |
| 5,182,707 | A | 1/1993 | Cooper et al. |
| 5,204,670 | A | 4/1993 | Stinton |
| 5,222,020 | A | 6/1993 | Takeda |
| 5,227,874 | A | 7/1993 | Von Kohorn |
| 5,228,450 | A | 7/1993 | Sellers |
| 5,231,990 | A | 8/1993 | Gauglitz |
| 5,249,044 | A | 9/1993 | Von Kohorn |
| 5,251,126 | A | 10/1993 | Kahn et al. |
| 5,261,401 | A | 11/1993 | Baker et al. |
| 5,262,943 | A | 11/1993 | Thibado et al. |
| 5,265,888 | A | 11/1993 | Yamamoto et al. |
| 5,266,179 | A | 11/1993 | Nankai et al. |
| 5,275,159 | A | 1/1994 | Griebel |
| 5,282,950 | A | 2/1994 | Dietze |
| 5,299,121 | A | 3/1994 | Brill et al. |
| 5,301,105 | A | 4/1994 | Cummings, Jr. |
| 5,304,468 | A | 4/1994 | Phillips |
| 5,307,263 | A | 4/1994 | Brown |
| 5,309,919 | A | 5/1994 | Snell et al. |
| 5,329,459 | A | 7/1994 | Kaufman et al. |
| 5,329,608 | A | 7/1994 | Bocchiere et al. |
| 5,331,549 | A | 7/1994 | Crawford, Jr. |
| 5,339,821 | A | 8/1994 | Fujimoto |
| 5,341,291 | A | 8/1994 | Roizen et al. |
| 5,343,239 | A | 8/1994 | Lappington et al. |
| 5,344,324 | A | 9/1994 | O'Donnell et al. |
| 5,357,427 | A | 10/1994 | Langen et al. |
| 5,366,896 | A | 11/1994 | Margrey et al. |
| 5,371,687 | A | 12/1994 | Holmes, II et al. |
| 5,375,604 | A | 12/1994 | Kelly et al. |
| 5,377,100 | A | 12/1994 | Pope et al. |
| 5,390,238 | A | 2/1995 | Kirk et al. |
| 5,399,821 | A | 3/1995 | Inagaki et al. |
| 5,410,471 | A | 4/1995 | Alyfuku et al. |
| 5,410,474 | A | 4/1995 | Fox |
| 5,429,140 | A | 7/1995 | Burdea et al. |
| 5,431,691 | A | 7/1995 | Snell et al. |
| 5,434,611 | A | 7/1995 | Tamura |
| 5,438,607 | A | 8/1995 | Przygoda, Jr. et al. |
| 5,441,047 | A | 8/1995 | David et al. |
| 5,454,721 | A | 10/1995 | Kuch |
| 5,454,722 | A | 10/1995 | Holland et al. |
| 5,456,606 | A | 10/1995 | McIntyre |
| 5,456,692 | A | 10/1995 | Smith, Jr. et al. |
| 5,458,123 | A | 10/1995 | Unger |
| 5,467,269 | A | 11/1995 | Flaten |
| 5,471,039 | A | 11/1995 | Irwin, Jr. et al. |
| 5,483,276 | A | 1/1996 | Brooks et al. |
| 5,488,412 | A | 1/1996 | Majeti et al. |
| 5,488,423 | A | 1/1996 | Walkingshaw et al. |
| 5,501,231 | A | 3/1996 | Kaish |
| 5,502,636 | A | 3/1996 | Clarke |
| 5,502,726 | A | 3/1996 | Fischer |
| 5,504,519 | A | 4/1996 | Remillard |
| 5,517,405 | A | 5/1996 | McAndrew et al. |
| 5,518,001 | A | 5/1996 | Snell |
| 5,519,433 | A | 5/1996 | Lappington et al. |
| 5,544,649 | A | 8/1996 | David et al. |
| 5,546,943 | A | 8/1996 | Gould |
| 5,549,117 | A | 8/1996 | Tacklind et al. |
| 5,550,575 | A | 8/1996 | West et al. |
| 5,553,609 | A | 9/1996 | Chen |
| 5,558,638 | A | 9/1996 | Evers et al. |
| 5,564,429 | A | 10/1996 | Bornn et al. |
| 5,569,212 | A | 10/1996 | Brown |
| 5,572,421 | A | 11/1996 | Altman et al. |
| 5,574,828 | A | 11/1996 | Hayward et al. |
| 5,576,952 | A | 11/1996 | Stutman et al. |
| 5,590,648 | A | 1/1997 | Mitchell et al. |

| | | | | | |
|---|---|---|---|---|---|
| 5,596,994 | A | | 1/1997 | Bro | |
| 5,597,307 | A | | 1/1997 | Redford et al. | |
| 5,601,435 | A | | 2/1997 | Quy | |
| 5,613,495 | A | | 3/1997 | Mills et al. | |
| 5,619,991 | A | | 4/1997 | Sloane | |
| 5,624,265 | A | | 4/1997 | Redford et al. | |
| 5,628,309 | A | | 5/1997 | Brown | |
| 5,629,981 | A | | 5/1997 | Nerlikar | |
| 5,631,844 | A | | 5/1997 | Margrey et al. | |
| 5,633,910 | A | | 5/1997 | Cohen | |
| 5,640,953 | A | | 6/1997 | Bishop et al. | |
| 5,642,731 | A | | 7/1997 | Kehr | |
| 5,642,936 | A | | 7/1997 | Evans | |
| 5,666,487 | A | | 9/1997 | Goodman et al. | |
| 5,670,711 | A | | 9/1997 | Detournay et al. | |
| 5,675,635 | A | | 10/1997 | Vos et al. | |
| 5,678,562 | A | | 10/1997 | Sellers | |
| 5,678,571 | A | | 10/1997 | Brown | |
| 5,687,322 | A | | 11/1997 | Deaton et al. | |
| 5,687,717 | A | | 11/1997 | Halpern et al. | |
| 5,687,734 | A | | 11/1997 | Dempsey et al. | |
| 5,704,364 | A | | 1/1998 | Saltzstein et al. | |
| 5,704,366 | A | | 1/1998 | Tacklind et al. | |
| 5,704,902 | A | | 1/1998 | Vandenbelt et al. | |
| 5,711,297 | A | | 1/1998 | Iliff | |
| 5,715,451 | A | | 2/1998 | Marlin | |
| 5,715,823 | A | | 2/1998 | Wood et al. | |
| 5,717,913 | A | | 2/1998 | Driscoll | |
| 5,720,733 | A | | 2/1998 | Brown | |
| 5,722,418 | A | | 3/1998 | Bro | |
| 5,727,153 | A | | 3/1998 | Powell | |
| 5,730,124 | A | | 3/1998 | Yamauchi | |
| 5,732,696 | A | | 3/1998 | Rapoport et al. | |
| 5,732,709 | A | | 3/1998 | Tacklind et al. | |
| 5,734,413 | A | | 3/1998 | Lappington et al. | |
| 5,752,234 | A | | 5/1998 | Withers | |
| 5,760,771 | A | | 6/1998 | Blonder et al. | |
| 5,772,585 | A | | 6/1998 | Lavin et al. | |
| 5,778,882 | A | | 7/1998 | Raymond et al. | |
| 5,782,814 | A | | 7/1998 | Brown et al. | |
| 5,785,650 | A | | 7/1998 | Akasaka et al. | |
| 5,791,342 | A | | 8/1998 | Woodard | |
| 5,792,117 | A | | 8/1998 | Brown | |
| 5,793,969 | A | | 8/1998 | Kamentsky et al. | |
| 5,796,393 | A | | 8/1998 | MacNaughton | |
| 5,802,494 | A | | 9/1998 | Kuno | |
| 5,810,747 | A | | 9/1998 | Brudny et al. | |
| 5,819,735 | A | | 10/1998 | Mansfield et al. | |
| 5,822,544 | A | | 10/1998 | Chaco et al. | |
| 5,822,715 | A | * | 10/1998 | Worthington et al. | 702/19 |
| 5,825,283 | A | | 10/1998 | Camhi | |
| 5,827,180 | A | | 10/1998 | Goodman | |
| 5,828,943 | A | | 10/1998 | Brown | |
| 5,835,896 | A | | 11/1998 | Fisher et al. | |
| 5,840,020 | A | * | 11/1998 | Heinonen et al. | 600/309 |
| 5,868,669 | A | | 2/1999 | Iliff | |
| 5,875,432 | A | | 2/1999 | Sehr | |
| 5,879,163 | A | | 3/1999 | Brown et al. | |
| 5,893,077 | A | | 4/1999 | Griffin | |
| 5,893,098 | A | | 4/1999 | Peters et al. | |
| 5,897,493 | A | | 4/1999 | Brown | |
| 5,899,855 | A | | 5/1999 | Brown | |
| 5,911,687 | A | | 6/1999 | Sato et al. | |
| 5,913,310 | A | | 6/1999 | Brown | |
| 5,918,603 | A | | 7/1999 | Brown | |
| 5,920,477 | A | | 7/1999 | Hoffberg et al. | |
| 5,933,136 | A | | 8/1999 | Brown | |
| 5,941,829 | A | | 8/1999 | Saltzstein et al. | |
| 5,961,446 | A | | 10/1999 | Beller et al. | |
| 5,971,922 | A | * | 10/1999 | Arita et al. | 600/365 |
| 5,983,217 | A | | 11/1999 | Khosravi-Sichani et al. | |
| 5,987,471 | A | | 11/1999 | Bodine et al. | |
| 5,995,969 | A | | 11/1999 | Lee et al. | |
| 5,997,476 | A | | 12/1999 | Brown | |
| 6,001,065 | A | | 12/1999 | DeVito | |
| 6,022,315 | A | | 2/2000 | Iliff | |
| 6,022,615 | A | | 2/2000 | Rettenbacher | |
| 6,024,281 | A | | 2/2000 | Shepley | |
| 6,029,138 | A | | 2/2000 | Khorasani et al. | |
| 6,035,328 | A | | 3/2000 | Soukal | |
| 6,046,761 | A | | 4/2000 | Echerer | |
| 6,049,794 | A | | 4/2000 | Jacobs et al. | |
| 6,050,940 | A | | 4/2000 | Braun et al. | |
| 6,055,314 | A | | 4/2000 | Spies et al. | |
| 6,055,487 | A | | 4/2000 | Margery et al. | |
| 6,055,506 | A | | 4/2000 | Frasca, Jr. | |
| 6,057,758 | A | | 5/2000 | Dempsey et al. | |
| 6,110,148 | A | | 8/2000 | Brown et al. | |
| 6,138,145 | A | | 10/2000 | Kawanaka | |
| 6,151,586 | A | | 11/2000 | Brown | |
| 6,168,563 | B1 | | 1/2001 | Brown | |
| 6,177,940 | B1 | | 1/2001 | Bond et al. | |
| 6,189,029 | B1 | | 2/2001 | Fuerst | |
| 6,221,012 | B1 | | 4/2001 | Maschke et al. | |
| 6,248,065 | B1 | | 6/2001 | Brown | |
| 6,368,273 | B1 | | 4/2002 | Brown | |
| 6,370,513 | B1 | | 4/2002 | Kolawa et al. | |
| 6,436,036 | B1 | | 8/2002 | Miller-Kovach et al. | |
| 6,513,532 | B2 | | 2/2003 | Mault et al. | |

FOREIGN PATENT DOCUMENTS

| | | |
|---|---|---|
| EP | 0286456 | 10/1988 |
| EP | 0320749 | 2/1989 |
| EP | 370599 | 5/1990 |
| EP | 0461910 | 12/1991 |
| EP | 508912 | 10/1992 |
| EP | 526166 | 2/1993 |
| EP | 0653718 | 11/1994 |
| EP | 676709 | 10/1995 |
| EP | 680727 | 11/1995 |
| EP | 761160 | 3/1997 |
| GB | 2218831 | 11/1989 |
| GB | 2225637 | 6/1990 |
| WO | WO-8501667 | 4/1985 |
| WO | WO-90/00367 | 1/1990 |
| WO | WO-9109374 | 6/1991 |
| WO | WO-93/01489 | 1/1993 |
| WO | WO-9302622 | 2/1993 |
| WO | WO-9416774 | 8/1994 |
| WO | WO-95/09386 | 4/1995 |
| WO | WO-95/20199 | 7/1995 |
| WO | WO-9529447 | 11/1995 |
| WO | WO-96/07908 | 3/1996 |
| WO | WO-96/25877 | 8/1996 |
| WO | WO-97/08605 | 3/1997 |
| WO | WO-97/12544 | 4/1997 |
| WO | WO-98/16895 | 4/1998 |

OTHER PUBLICATIONS

"Central Fetal Monitoring Systems ewith Optical Disk Storage", *New Technology Brief,* (Nov./Dec. 1988), vol. 2, No. 6, pp. 249-251.

"European Search Report", From 6858P005EP,(Mar. 27, 1998).

"How Flash Memory Works", Internet printout of URL address: http://www.howstuffworks.com/flash-memory4.htm, (Sep. 28, 2002),2 pages.

"Introducing the Next Generation of About Your Diabetes", *U.S. Pharmacopcial Convention and American Diabetes Association,* (1993).

"The description of the Tandy Radio Shack TRS-80 Model 100/102 device available at http://www.old-computers.com/museum/computer.asp?c=233", *World Wide Web,* (Feb. 13, 2004),1-3.

Anonymous, "Health Hero netowrk, inc. Receives First-Ever FDA Clearance for Connecting Medical Devices to Internet", *PR Newswire,* (Dec. 2, 1999),3 pages.

Billiard, A. , et al., "Telematic Transmission of Computerized Blood Glucose Profiles for IDDM Patients", *Diabetes Care,* (Feb. 1991), vol. 14, No. 2, pp. 130-134.

Bower, "Brain Clues to Energy-efficient Learning", *Science News,* (Apr. 1992),v 141; p. 215(1); Dialog: File 647, Acct# 12123949.

Bruce, "Health Hero Network CEO, CNNfn", *Digital Jam,* (Dec. 1, 1999),3 pages.

Bruce, et al., "The Effects of Sympathetic Nervous System Activation and Psychological Stress . . . ", *Diabetologia,* (1992),. ; ; 35 (9); 835-843; Dialog: File 5, Acc# 9629427.

Brunetti, P. , et al., "A Simulation Study on a Self-Tuning Portable Controller of Blood Glucose", *The International Journal of Artifical Organs,* (1993), vol. 16, No. 16, pp. 51-57.
Caprihan, A. , et al., "A Simple Microcomputer for Biomedical Signal Processing", *IECI '78 Annual Conference Proceedings on Industrial Applications of Microprocessors,* (Mar. 20, 1978), 18-23.
Cheng, Joe H., "PCT Search Report", (Jan. 11, 1996).
Douglas, A. S., et al., "Hand-Held Glucose Monitor and Recorder", *Proceedings of the Annual International Conference of the IEEE Engineering in Medicine and Biology Society,* New Orleans, LA,(Nov. 1988),pp. 747-748.
Fabietti, P. G., et al., "Wearable System for Acquisition, Processing and Storage of the Signal from Amperometric Glucose Sensors", *The International Journal of Artificial Organs,* (1991),vol. 14, No. 3, pp. 175-178.
Finston, "Parent + Teacher = Healthy Child", *Diabetes Forecast,* (Apr. 1994),v47 n9; p. 26(5); Dialog: file 149, Acc# 15804228.
Fox, "Not My Type: Type B Behavior, Type I Diabetes Plus Stress Equals Blood Sugar Blues", *Health,* (Mar. 1988),v20 n3; pp. 22(1); Dialog: File 149, Acc#06397959.
Frieberger, Paul , "Video Game Takes on Diabetes Superhero "Captain Novolin" Offers Treatment Tips", *San Francisco Examiner,* (Jun. 26, 1992),Fourth Edition, Business Section B1.
Giuffrida, Antonio , et al., "Should We Pay the Patient? Review of Financial Incentives to enhance Patient compliance", *Biomedical Journal,* (1997), vol. 315, pp. 703-707.
Hauben, Jay R., "A Brief History of the Cleveland Free-Net", available at http://www.ais.org/~irh/acn7-1.a09.html, (1995),pp. 1-4.
Hauser, Thomas , et al., "Will Computers Replace or Complement the Diabetes Educator?", *The Medical Journal of Australia,* (Oct. 5, 1992),vol. 157, 489-491.
Horio, Hiroyuki, et al., "Clinical Telecommunication Network System for Home Monitoring", *Medical & Biological Engineering & Computing,* (Mar. 1994), vol. 32, 227-230.
Hunter, "Technological Advances in Bedside Monitoring: Biosensors", *Archives and Laboratory Medicine,* (Jul. 1987),pp. 633-636.
Kauffmann, Francine , et al., "Epidermiological Study of the Genetics and Environment of Asthma, Bronchial Hyperresponsiveness and Atopy", *Am. J. Respir. Crit. Care Med.,* (1997), vol. 156, pp. S123-S129.
Kaufman, Steven , "B., The Learning Game", *Nation's Business,* (Nov. 1993).
Kuykendall, V G., et al., "Assessment of Self-Monitored Blood Glucose results Using a Reflectance Meter with Memory and Microcomputer", *Symposium on Computer Applications in Medical Care,* (Jan. 1981),vol. 70, pp. 98 -102.
Lacyk, John , "PCT Search Report", (Jun. 12, 1997).
Latman, N. S., "Evaluation of Electronic, Digital Blood Glucose Monitors", *Biomedical Instrumentation and Technology,* (1991),vol. 25, No. 1, 43-49.
Laughton, Miles E., "A Portable Microcomputer for Long-Term Physiological Monitoring in the Home and Work Environment", *Medical Monitoring in the Home and Work Environment,* (1990),pp. 47-57.
Leyerle, Beverly J., et al., "The PDMS as a Focal Point for Distributed Patient Data", *International Journal of Clinical Monitoring and Computing,* (1988), vol. 5, pp. 155-161.
Makikawa, M. , et al., "Microprocessor-Based Memory Device for Ambulatory Heart Rate and Physical Activity Recording", *Methods of Information in Medicine,* (1994), vol. 33, No. 1, pp. 94-96.
Marsh, David G., "Approaches Toward the Genetic Analysis of Complex Traits Asthma and Atopy", *Am. J. Respir.Crit.Care Med.,* (1997),vol. 156, pp. S-133-S138.
Martinez, Fernando D., "Complexities of the Genetics of Asthma", *Am. J. Respir. Crit. Care Med.,* (1997),vol. 156, pp. S117-S122 .
Mazzola, et al., "Video Diabetes: A Teaching Tool for Children with Insulin-Dependent Diabetes", *Proceedings—7th Annual Symposium on Computer Applications in Medical Care; Washington, DC; Dialog:,* (Oct. 1983),File 8, Acc# 01624462.
Meissner, et al., "Building an Integrated Clinical and Research Network", *Proceedings of the SPIE,* (Oct. 24, 1995),vol. 2618, p. 92 99.
Moore, "New Applications Break Through Storage Boundaries", *Computer Technology Review,* (Oct. 1999),vol. 19, No. 10, p. 1.
Pfeiffer, E. F., "The Glucose Sensor: The Missing Link in Diabetes Therapy", *Hormone and Metabolic Research,* (1990),vol. 24, Suppl., pp. 154-164.
Poitout, V. , et al., "A Glucose Mointoring System for On Line Estimation in Man of Blood Glucose Concentration Using a Miniaturized Glucose Sensor Implanted in the Subcutaneous Tissue and a Wearable Control Unit", *Diabetologia,* (1993),vol. 36, pp. 658-663.
Potter, David , "Fundamentals of PC-Based Data Acquisition", *Sensors,* (Feb. 1994),pp. 12-20.
Reis, Howard , "Telemedicine: Transmitting Expertise to the Point of Care",*Proceedings: Toward an Electronic Patient Record,* (1997),pp. 248-256.
Roberts;, "Diabetes and Stress: A Type A Connection?", *Psychology Today,* (Jul. 1987),v. 21; pp. 22(1); Dialog: File 149, Acc# 05038381.
Rose, V. L., et al., "Decentralized Testing for Prothrombin Time and Activated Partial Thromboplastin Time Using a Dry Chemistry Portable Analyser", *Archives of Pathology and Laboratory Medicine,* (Jun. 1993),vol. 117, pp. 611-617.
Schenkels, P. , "Supplementary European Search Report", Application No. EP 97 92 2716,(Mar. 11, 2002).
Schork, Nicholas J., "Genetics of Complex Disease", *Am. J. Respir. Crit. Care Med.,* (1997),vol. 156, pp. s103-S109.
Schrezenmeir, J. , et al., "Computer Assisted Insulin Dosage Adjustment—Perspective for Diabetes Control", *Hormone and Metabolic Research, Supplement Series,* (1990),vol. 24, pp. 116-123.
Shandle, Jack , "Who Will dominate the desktop In the 90s?", *Electronics,* (Feb. 1990),pp. 48-50.
Shults, Marc C., et al., "A Telemetry-Instrumentation System for Monitoring Multiple Subcutaneously Implanted Glucose Sensors", *IEEE Transactions on Biomedical Engineering,* (Oct. 1994),vol. 41, No. 10, pp. 937-942.
Soeldner, J. S., "Treatment of Diabetes Mellitus by Devices", *The American Journal of Medicine,* (Jan. 1981),vol. 70, 183-194.
Updike, Stuart J., et al., "Laboratory Evaluation of New Resusable Blood Glucose Sensor", *Diabetes Care,* (Nov./Dec. 1988),vol. 11, No. 10, pp. 801-807.
Vallera, D. A., et al., "Accuracy of Portable Blood Glucose Monitoring", *American Journal of Clinical Pathology,* (1991),vol. 95, No. 2, pp. 247-252.
Voelker, Rebecca , "Shoe Leather Therapy is Gaining on TB", *Jama,* (Mar. 13, 1996),vol. 275, 743.
Wyatt, J. C., "Clinical Data Systems, Part 2: Components and Techniques", *Lancet,* ( Dec. 1994),vol. 344, No. 8937, pp. 1609-1614.
Yoshizawa, Daisuke , et al., "The Development of a Data Processing System with Personal Computer MSX Standard System for Flow Injection Analysis", *Journal of Flow Injection Analysis,* (1988),V. 5, No. 2. pp. 101-110.

* cited by examiner

TABLE 1

| TIME AFTER INFECTION (MINUTES) | $F_k(t)$ |
|---|---|
| 0 | 1.00 |
| 15 | 0.98 |
| 30 | 0.97 |
| 45 | 0.96 |
| 60 | 0.94 |
| 75 | 0.90 |
| 90 | 0.86 |
| 105 | 0.82 |
| 120 | 0.78 |
| 135 | 0.70 |
| 150 | 0.64 |
| 165 | 0.58 |
| 180 | 0.52 |
| 195 | 0.48 |
| 210 | 0.44 |
| 225 | 0.40 |
| 240 | 0.36 |
| 255 | 0.30 |
| 270 | 0.28 |
| 285 | 0.26 |
| 300 | 0.24 |
| 315 | 0.22 |
| 330 | 0.20 |
| 345 | 0.19 |

*FIG. 6A*

TABLE 1 (CONT.)

| TIME AFTER INFECTION (MINUTES) | $F_k(t)$ |
|---|---|
| 360 | 0.18 |
| 380 | 0.17 |
| 400 | 0.16 |
| 420 | 0.15 |
| 440 | 0.14 |
| 460 | 0.13 |
| 480 | 0.12 |
| 500 | 0.11 |
| 520 | 0.10 |
| 540 | 0.09 |
| 560 | 0.08 |
| 580 | 0.07 |
| 600 | 0.06 |
| 620 | 0.05 |
| 640 | 0.04 |
| 660 | 0.03 |
| 680 | 0.02 |
| 700 | 0.01 |
| > 720 | 0.00 |

*FIG. 6B*

TABLE 2

| TIME AFTER INFECTION (MINUTES) | $F_k(t)$ |
|---|---|
| 0 | 1.00 |
| 15 | 0.97 |
| 30 | 0.93 |
| 45 | 0.90 |
| 60 | 0.85 |
| 75 | 0.80 |
| 90 | 0.70 |
| 105 | 0.60 |
| 120 | 0.52 |
| 135 | 0.46 |
| 150 | 0.40 |
| 165 | 0.32 |
| 180 | 0.28 |
| 195 | 0.22 |
| 210 | 0.16 |
| 225 | 0.14 |
| 240 | 0.12 |
| 255 | 0.10 |
| 270 | 0.08 |
| 285 | 0.07 |
| 300 | 0.06 |
| 315 | 0.05 |
| 330 | 0.04 |
| 345 | 0.03 |
| 360 | 0.02 |
| 375 | 0.01 |
| > 390 | 0.00 |

*FIG. 7*

DIABETES MANAGEMENT SYSTEM AND METHOD FOR CONTROLLING BLOOD GLUCOSE

Matter enclosed in heavy brackets [ ] appears in the original patent but forms no part of this reissue specification; matter printed in italics indicates the additions made by reissue.

CONTINUATION APPLICATION INFORMATION

This application is a *continuation-in-part of application Ser. No. 08/844,245 filed Apr. 18, 1997, now U.S. Pat. No. 5,822,715 which is a* continuation in part of application Ser. No. 08/781,278 filed Jan. 10, 1997, now U.S. Pat. No. 5,956, 501 [which]. *Application Ser. No. 08/781,278* is hereby incorporated by reference.

FIELD OF THE INVENTION

The present invention relates generally to disease management systems, and in particular to a diabetes management system for predicting a future blood glucose value of a patient and for recommending a corrective action to the patient when the future blood glucose value lies outside of a target range.

DESCRIPTION OF PRIOR ART

Insulin dependent diabetes mellitus (IDDM) is caused by the auto-immune destruction of the insulin producing islets of Langerhans in the pancreas. Insulin replacement therapy is the interim treatment for IDDM until such time as islet transplants become feasible. Insulin lowers the concentration of glucose in the blood, while food raises the concentration of glucose in the blood. The challenge of insulin therapy is to administer food and insulin in a manner which maintains blood glucose concentrations in an acceptable range, thereby avoiding hypoglycemia and hyperglycemia.

Hyperglycemia has adverse long term consequences for the body. These consequences include kidney damage leading to kidney failure, micro-enurisms in the retina causing blindness, and the blocking of capillaries in the extremities causing an inability to heal wounds and subsequent gangrene. Hypoglycemia has an immediate adverse consequence of reduced brain function which leads to confusion and an inability to reason, remember, or react. In the extreme, hypoglycemia causes seizure, coma, and death.

The first insulin used by diabetes patients was regular insulin taken from beef or pig pancreases. This insulin lasts for about six hours, so that patients were required to inject it three or four times per day. After World War II, longer acting insulin was developed by binding regular insulin to protamine and zinc. Regular insulin dissociates slowly from protamine and zinc, extending insulin action to twelve hours for intermediate acting insulin and twenty-four hours for ultra-lente insulin. Patients enjoyed reducing injections to one per day, but were required to modify their eating to a snack-all-day regimen to avoid hypoglycemia. The one daily insulin dose was adjusted as needed to reduce the incidence of both hypoglycemia and hyperglycemia.

The development of portable blood glucose meters encouraged the development of more sophisticated insulin therapy regimens. One of these regimens is the split/mixed regimen which consists of two daily doses of mixed regular and intermediate acting insulins taken before breakfast and dinner. These four insulin therapy components are adjusted using blood glucose values measured before each meal and at bedtime. Patients using the split/mixed regimen are required to eat substantially the same meals every day so that the four insulin components may be adapted to the consistent meal pattern over time.

The split/mixed regimen has the advantage of allowing independent adjustment of insulin doses for each meal and requires only two injections per day. However, it has several disadvantages which are primarily due to the intermediate acting insulin components. The intermediate acting insulin taken before breakfast affects lunch time and pre-dinner blood glucose, requiring a patient to commit to the size and timing of lunch before eating breakfast. The broad action of the intermediate acting insulin may lead to hypoglycemia before or after lunch when the size or timing of the lunch is varied. Similarly, the intermediate acting insulin taken before dinner requires the patient to eat a snack at bedtime to mitigate nocturnal hypoglycemia. Even when a snack is eaten, the intermediate acting insulin may cause hypoglycemia around 3 AM when its action peaks.

Many of the disadvantages of the split/mixed regimen are overcome in a second insulin therapy regimen called the basal/bolus regimen. The basal/bolus regimen attempts to emulate the method by which an intact pancreas controls blood glucose. Normally, the intact pancreas produces a steady supply of basal insulin to accommodate the body's basic resting needs. The pancreas handles meals by releasing a sharp impulse of bolus insulin in a first phase. The sharp impulse of bolus insulin raises circulating insulin levels immediately. The first phase is followed by a sustained level of heightened insulin release in a second phase. The second phase continues until the body's blood glucose concentration falls back to normal, at which point basal levels are obtained once again.

In the basal/bolus regimen, the basal insulin releases are emulated by two daily basal injections of intermediate acting insulin, such as Lente or Neutral Protamine Hagedorn (NPH), generally taken before breakfast and at bedtime. The bolus insulin releases are emulated by bolus injections of regular or fast acting lispro insulin taken before each meal. Fast acting lispro insulin allows the bolus injections to emulate the first phase action of the pancreas better than regular insulin by reducing the delay before the insulin injection takes effect and by shortening the overall duration of the insulin's action.

Thus, the basal/bolus regimen generally includes four insulin doses per day consisting of a pre-breakfast dose of intermediate insulin combined with regular or lispro insulin, pre-lunch and pre-dinner doses of regular or lispro insulin, and a bedtime dose of intermediate insulin. The two basal insulin doses accommodate the basic insulin needs of a patient absent any perturbations due to food. Food is handled by the bolus insulin doses, which the patient attempts to tailor to the amount of food to be eaten.

Problems arise in the basal/bolus regimen when a patient incorrectly estimates the dose of bolus insulin required for a given meal. Too little insulin causes the patient to develop hyperglycemia, while too much insulin causes the patient to develop hypoglycemia. Hypoglycemia or hyperglycemia may also result when the size of the meal is varied without adequate adjustment of the bolus insulin dose. Patients using the basal/bolus regimen are typically required to eat substantially the same meals every day so that the bolus insulin doses may be adapted to the consistent meal pattern over time.

Several electronic diabetes management systems have been developed to assist patients in the implementation of the split/mixed or basal/bolus regimens. One such system is disclosed in U.S. Pat. No. 5,019,974 issued to Beckers on May 28, 1991. Beckers describes a master computer for developing a therapy program for a patient and for downloading the therapy program to a patient-operated recorder. The recorder reminds the patient of any therapy due and records that the therapy has been performed by the patient. Data from the recorder is subsequently fed back to the master computer to improve or alter the therapy program.

In using Backers' system, a patient must strictly adhere to the predetermined therapy guidelines in order for the therapy program to be effective. To make any therapy adjustments, the patient must upload data to the master computer, wait for the therapy adjustments, and strictly follow the adjusted guidelines. Thus, Beckers' system restricts the patient to a consistent meal plan, with no flexibility for adjusting the therapy program to meals of varying size or timing.

Following a consistent meal plan is extremely difficult, whether for diabetes treatment or weight loss. Rarely can a patient stick to a predetermined meal plan every day of his or her life. Consequently, Beckers' system is ineffective for assisting the patient in controlling blood glucose and avoiding hypoglycemia or hyperglycemia when the patient deviates from the plan during his or her normal course of behavior.

Moreover, Beckers' system lacks any mechanism for predicting the patient's future blood glucose concentration and is thus unable to alert the patient to future hypoglycemia or hyperglycemia resulting from an unusual meal or an incorrectly estimated insulin dose taken for the meal. Further, Beckers does not teach or describe any mechanism for recommending to the patient a corrective action, such as a supplemental insulin dose or carbohydrate supplement, when the patient has a potential for future hypoglycemia or hyperglycemia.

Another diabetes management system is disclosed in U.S. Pat. No. 4,731,726 issued to Allen on Mar. 15, 1988. Allen describes a system which includes a physician computer for downloading therapy guidelines to a patient-operated apparatus. The apparatus includes a blood glucose meter for recording a patient's blood glucose values and keys for entering patient data relating to diet, insulin, exercise, stress, and symptoms of illness. The apparatus is programmed to recommend insulin doses to the patient based upon the data supplied.

Unfortunately, Allen's system recommends insulin doses to the patient based upon pre-meal blood glucose values only, as stated in column 16, lines 42-44. This forces the patient to wait until the next meal before he or she may take action to correct hypoglycemia or hyperglycemia developed since the previous meal. Further, Allen's system has no mechanism for predicting the patient's future blood glucose concentration based upon the patient's post-meal blood glucose value and the insulin action remaining from insulin doses injected before the meal. As a result, Allen's system is unable to alert the patient to future hypoglycemia or hyperglycemia resulting from the patient eating an unusual meal or taking an incorrect insulin dose for the meal.

OBJECTS AND ADVANTAGES OF THE INVENTION

In view of the above, it is an object of the present invention to provide a diabetes management system for predicting a future blood glucose concentration of a patient based upon the patient's current blood glucose concentration and the insulin action remaining from previous insulin doses, thereby enabling the patient to take timely corrective action to prevent hypoglycemia or hyperglycemia. It is another object of the invention to provide a diabetes management system for recommending the corrective action to the patient when the predicted blood glucose value lies outside of a target range.

These and other objects and advantages will become more apparent after consideration of the ensuing description and the accompanying drawings.

SUMMARY

The invention presents a system and method for assisting a patient having diabetes mellitus in controlling blood glucose. The system includes a patient-operated apparatus having a blood glucose meter for measuring a blood sample of the patient and for producing from a measurement of the blood sample a blood glucose value $G(t_d)$ representative of a blood glucose concentration of the patient at time $t_d$. The apparatus also includes a user interface for entering in the apparatus an insulin dose value $I_k$ representative of an insulin dose administered to the patient prior to time $t_d$.

The apparatus further includes a memory for storing maximum and minimum values defining a target blood glucose range of the patient. The memory also stores a target blood glucose value of the patient within the range, an insulin sensitivity value representative of an insulin sensitivity of the patient, and information for determining an insulin action value $F_k(t_d)$ representative of a fraction of insulin action remaining at time $t_d$ from the insulin dose.

A processor is connected to the glucose meter, user interface, and memory. The processor is programmed to determine the insulin action value $F_k(t_d)$ and to determine a future blood glucose value $G(t_j)$ representative of an expected blood glucose concentration of the patient at time $t_j$. The processor determines the future blood glucose value $G(t_j)$ in dependence upon the blood glucose value $G(t_d)$, the insulin dose value $I_k$, the insulin sensitivity value, and the insulin action value $F_k(t_d)$. The processor is also programmed to determine a corrective action for the patient when the future blood glucose value $G(t_j)$ lies outside of the target range.

The corrective action is preferably an administration of a supplemental insulin dose when the future blood glucose value $G(t_j)$ lies above the target range or a consumption of a number of grams of carbohydrates when the future blood glucose value $G(t_j)$ lies below the target range. The processor is programmed to determine the supplemental insulin dose in dependence upon the insulin sensitivity value and a difference between the future blood glucose value $G(t_j)$ and the target blood glucose value. The processor is further programmed to determine the number of grams of carbohydrates to be consumed in dependence upon the difference between the future blood glucose value $G(t_j)$ and the target blood glucose value. A display is connected to the processor for displaying the future blood glucose value $G(t_j)$ and for recommending the corrective action to the patient.

The system also includes a healthcare provider computer in communication with the apparatus for receiving from the apparatus blood glucose values and insulin dose values and for calculating from the values an adjusted insulin sensitivity value for the patient. The apparatus includes a communication device, such as a modem and input/output port, connected to the processor for establishing a communication link between the apparatus and the healthcare provider computer, for transmitting the blood glucose values and insulin dose values through the communication link, and for receiving through the communication link the adjusted insulin sensitivity value.

BRIEF DESCRIPTION OF THE DRAWINGS

FIG. 6A is a sample table showing fractions of insulin action remaining from a dose of regular insulin at corresponding time points after injection.

FIG. 6B is a continuation of the table of FIG. 6A.

FIG. 7 is a sample table showing fractions of insulin action remaining from a dose of fast acting insulin at corresponding time points after injection.

DETAILED DESCRIPTION

The present invention is a diabetes management system and method for predicting a future blood glucose value of a patient and for recommending to the patient a corrective action when the future blood glucose value lies outside of a target blood glucose range. In the following description, numerous specific details are set forth in order to provide a thorough understanding of the present invention. However, it will be apparent to one of ordinary skill in the art that these specific details need not be used to practice the invention. In other instances, well known structures, interfaces, and processes are not shown in detail to avoid unnecessarily obscuring the present invention.

Figure 1:
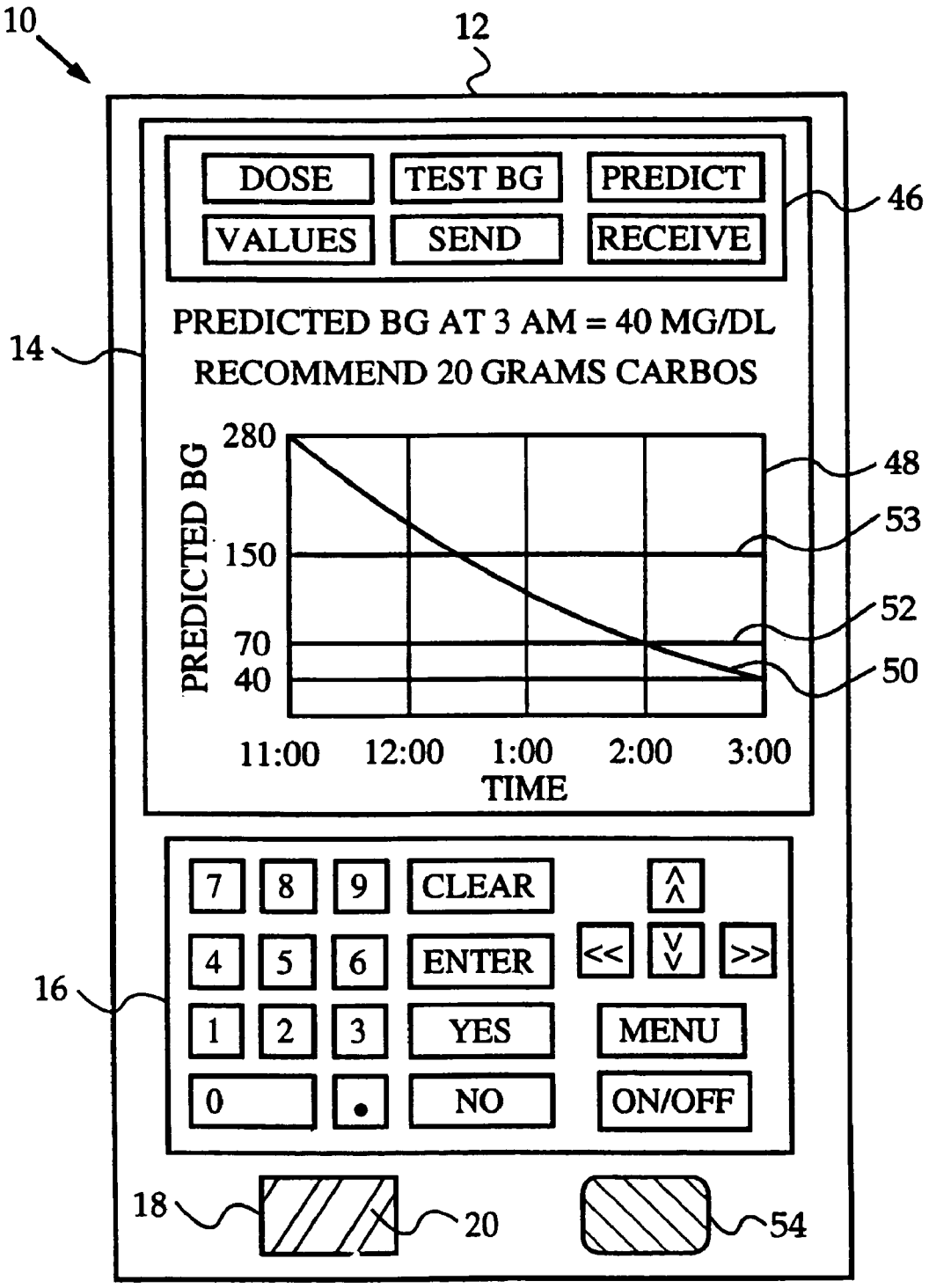
FIG. 1 is a top plan view of a patient-operated apparatus according to the invention.

FIGS. 1-7 illustrate a diabetes management system according to a preferred embodiment of the invention. Referring to FIG. 1, the diabetes management system includes a patient-operated apparatus 10 having a housing 12 for holding the components of apparatus 10. Housing 12 is preferably sufficiently compact to enable apparatus 10 to be hand-held and carried by a patient. A strip guide 18 for receiving a blood glucose test strip 20 is located on a surface of housing 12. Test strip 20 is for receiving a blood sample from the patient.

Apparatus 10 includes a display 14 for displaying predicted future blood glucose values and for recommending to the patient corrective actions when the future blood glucose values lie outside of a target blood glucose range. Display 14 is preferably a liquid crystal display (LCD). Display 14 is also designed to display prompts and a menu 46 to the patient during the operation of apparatus 10.

Menu 46 preferably includes a number of menu options as follows. The "DOSE" option starts a procedure for entering in apparatus 10 insulin dose values representative of insulin doses administered to the patient. Each insulin dose is typically self-injected by the patient. After injecting a dose, the patient selects the "DOSE" option to record in apparatus 10 the dose value and the type of insulin injected. The "TEST BG" option starts a procedure for measuring a current blood glucose value of the patient. The "PREDICT" option starts a procedure for predicting a future blood glucose value of the patient.

The "VALUES" option starts a procedure for entering in apparatus 10 various parameter values used to predict the future blood glucose values and to recommend appropriate corrective actions to the patient. The "SEND" option starts a procedure for transmitting the blood glucose values and insulin dose values stored in apparatus 10 to a healthcare provider computer. The "RECEIVE" option starts a procedure for receiving data from the healthcare provider computer.

Display 14 is also designed to display the predicted future blood glucose values in graphical form. Display 14 preferably displays a graph 48 which includes a blood glucose value curve 50 generated from the predicted blood glucose values. Graph 48 also includes a hypoglycemic line 52 indicating a hypoglycemic threshold of the patient and a hyperglycemic line 53 indicating a hyperglycemic threshold of the patient. Apparatus 10 also includes an audio transducer, such as a speaker 54, for audibly alerting the patient when a predicted future blood glucose value lies below the hypoglycemic threshold.

Apparatus 10 further includes a keypad 16 having a number of keys as follows. The ON/OFF key is pressed to turn apparatus 10 on and off. Number keys 0, 1, 2, 3, etc. are used for entering information on display 14, such as insulin dose values, insulin types, and dates and times of injections. The ENTER key is used after operation of the number keys to enter the information in apparatus 10. The ENTER key is also used to select menu options. The CLEAR key is used to clear numbers which have been entered incorrectly. The YES and NO keys are pressed in response to prompts on display 14 which require a yes or no answer.

The MENU key is pressed to display menu 46 on display 14. The ARROW keys are for scrolling through the menu options. Specific techniques for manufacturing and using an electronic apparatus having these keys are well known in the art. Further, those skilled in the art will recognize that the keys may be replaced by other user controls, such as switches, buttons, or graphic controls implemented on a touch sensitive screen.

Figure 2:
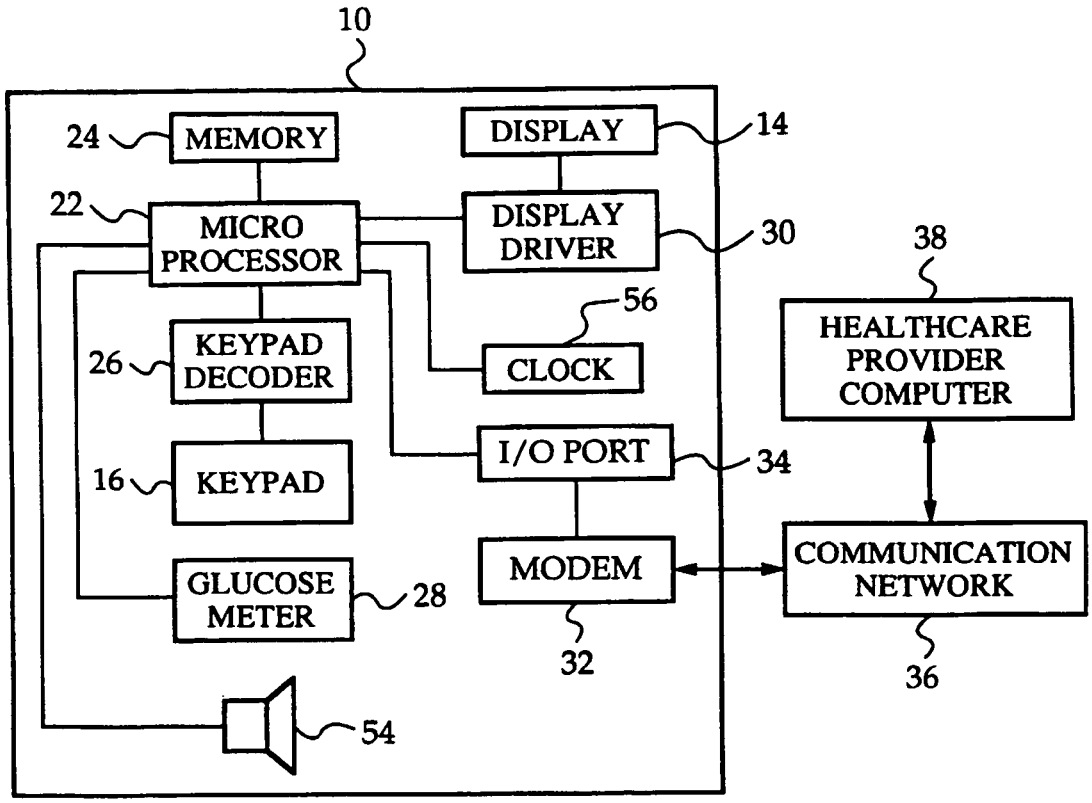
FIG. 2 is a schematic block diagram of the apparatus of FIG. 1 connected to a healthcare provider computer through a communication network.

FIG. 2 is a schematic block diagram illustrating apparatus 10 in greater detail. Apparatus 10 includes a microprocessor 22 and a memory 24 connected to microprocessor 22. Microprocessor 22 is designed to execute a computer program stored in memory 24 to perform the various calculations and control functions which are described in the operation section below.

Keypad 16 is connected to microprocessor 22 through a standard keypad decoder 26. Display 14 is connected to microprocessor 22 through a display driver 30. Microprocessor 22 communicates with display driver 30 via an interface, and display driver 30 updates and refreshes display 14 under the control of microprocessor 22. Speaker 54 and a clock 56 are also connected to microprocessor 22. Speaker 54 operates under the control of microprocessor 22 to emit audible tones alerting the patient to possible future hypoglycemia. Clock 56 supplies the current date and time to microprocessor 22.

Memory 24 also stores blood glucose values of the patient, the insulin dose values, the insulin types, and the parameter values used by microprocessor 22 to calculate future blood glucose values, supplemental insulin doses, and carbohydrate supplements. Each blood glucose value and insulin dose value is stored in memory 24 with a corresponding date and time. Memory 24 is preferably a nonvolatile memory, such as an electrically erasable read only memory (EEPROM).

Apparatus 10 also includes a blood glucose meter 28 connected to microprocessor 22. Glucose meter 28 is designed to measure blood samples received on blood glucose test strips and to produce blood glucose values from measurements of the blood samples. Such glucose meters are well known in the art. Glucose meter 28 is preferably of the type which produces digital values which are output directly to microprocessor 22. Alternatively, blood glucose meter 28 may be of the type which produces analog values. In this alternative embodiment, blood glucose meter 28 is connected to microprocessor 22 through an analog to digital converter (not shown).

Apparatus 10 further includes an input/output port 34, preferably a serial port, which is connected to microprocessor 22. Port 34 is connected to a modem 32 by an interface, preferably a standard RS232 interface. Modem 32 is for establishing a communication link between apparatus 10 and a healthcare provider computer 38 through a communication network 36. Modem 32 is capable of transmitting data to and receiving data from provider computer 38 through communication network 36. In the preferred embodiment, communication network 36 is a telephone network and modem 32 establishes the communication link to computer 38 through telephone lines.

Figure 3:
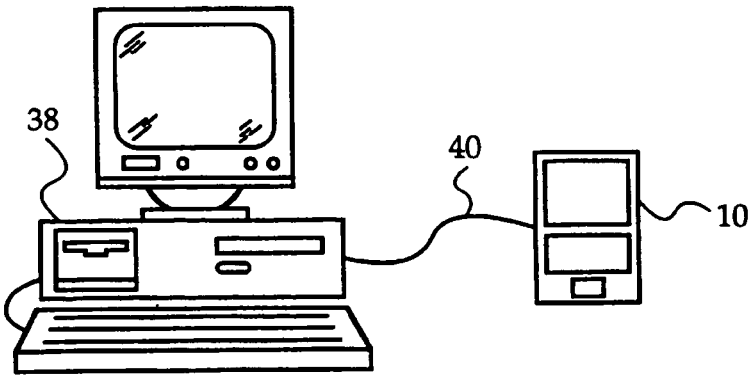
FIG. 3 is a schematic diagram of the apparatus of FIG. 1 connected to the healthcare provider computer of FIG. 2 through a connection cord.

Referring to FIG. 3, the input/output port may also be used to establish an alternative communication link between apparatus 10 and computer 38 through a data connection cord 40. Connection cord 40 is connectable to the input/output port of apparatus 10 and to a corresponding input/output port of healthcare provider computer 38. Specific techniques for connecting electronic devices through connection cords are well known in the art.

Healthcare provider computer 38 is preferably a personal computer located at a healthcare provider site, such as the office of the patient's physician. Healthcare provider computer 38 is designed to receive the patient's blood glucose values and insulin dose values from apparatus 10 and calculate from the values an adjusted insulin sensitivity value for the patient, as will be explained in the operation section below.

The computer program executed by microprocessor 22 includes equations for calculating future blood glucose values, supplemental insulin doses, and carbohydrate supplements. The variables used in the computer program are defined as follows:

$t_1, t_2, \ldots t_d, \ldots t_j \ldots. t_M$=time points.

$G(t_d)$=blood glucose value representative of a blood glucose concentration of the patient at time $t_d$.

$G(t_j)$=future blood glucose value representative of an expected blood glucose concentration of the patient at time $t_j$.

$I_k$=insulin dose value representative of an insulin dose k administered to the patient prior to time $t_d$, where k=1 to N and N=the total number of bolus and supplemental insulin doses administered to the patient. Insulin dose value $I_k$ is preferably expressed in units of insulin.

$P_k$=insulin type of insulin dose k, e.g. regular insulin or fast acting lispro insulin.

$F_k(t_d)$=insulin action value representative of the fraction of insulin action remaining at time $t_d$ from insulin dose k. For the purposes of this specification and the appended claims, insulin action is defined as the action of insulin to lower a patient's blood glucose concentration.

$F_k(t_j)$=insulin action value representative of a fraction of insulin action remaining at time $t_j$ from insulin dose k.

S=insulin sensitivity value representative of an insulin sensitivity of the patient. Insulin sensitivity value S indicates the amount a unit of insulin is expected to lower the patient's blood glucose concentration. Value S is a variable which is preferably updated in response to data collection from the patient, as described in detail below.

D=a recommended supplemental dose of insulin calculated for the patient. Dose D is preferably expresses in units of insulin.

C=carbohydrate value indicating the amount one gram of carbohydrates is expected to raise the patient's blood glucose concentration.

$R_{max}$,$R_{min}$=maximum and minimum values, respectively, defining a target blood glucose range of the patient.

T=target blood glucose value of the patient within the target blood glucose range.

H=Hypoglycemic value indicating a hypoglycemic threshold of the patient below which a carbohydrate supplement is desired.

B=the number of grams of carbohydrates to be consumed by the patient in a recommended carbohydrate supplement.

With these definitions, future blood glucose value $G(t_j)$ is calculated according to equation (1):

$$G(t_j) = G(t_d) - S\left[\sum_{k=1}^{N} I_k(F_k(t_d) - F_k(t_j))\right] \tag{1}$$

Microprocessor 22 calculates future blood glucose value $G(t_j)$ from blood glucose value $G(t_d)$, insulin sensitivity value S, insulin dose value $I_k$, and insulin action values $F_k(t_d)$ and $F_k(t_j)$. If the patient has injected multiple insulin doses, their remaining action is summed as shown. Blood glucose value $G(t_d)$ is preferably measured a sufficient time after the patient's last meal to ensure that most or all of the meal has already been absorbed. A sufficient time is usually two hours after a typical meal, or one hour after a snack or smaller meal.

Figure 4:
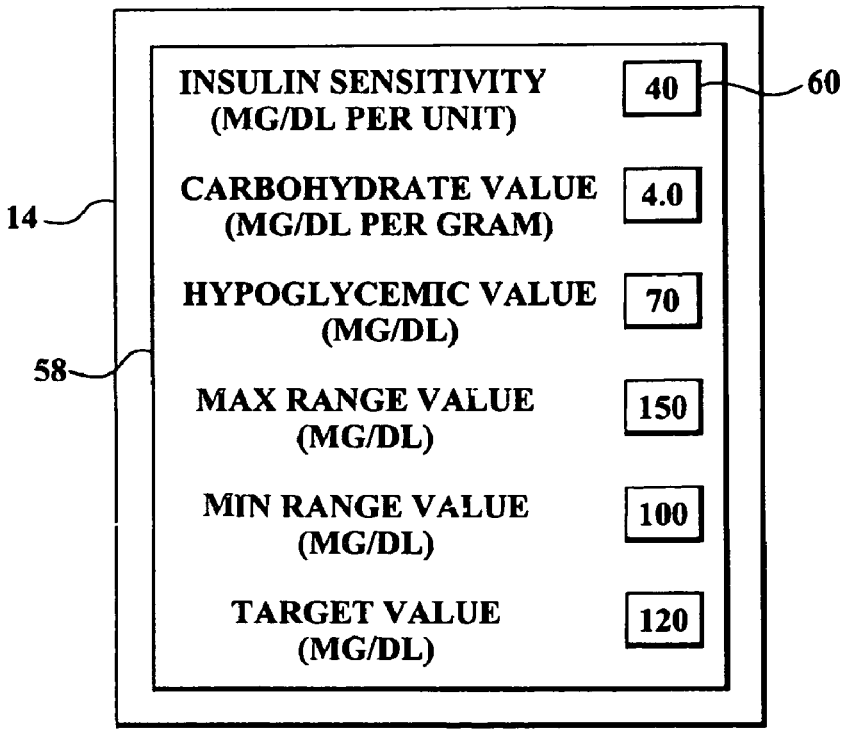
FIG. 4 is a sample parameter value entry window as it appears on a display of the apparatus of FIG. 1.

FIG. 4 shows a sample parameter value entry window 58 as it appears on display 14. Window 58 is preferably a pop-up window displayed when the patient selects the "VALUES" option from the menu. Window 58 includes data entry fields 60 for entering in apparatus 10 insulin sensitivity value S, carbohydrate value C, hypoglycemic value H, maximum value $R_{max}$, minimum value $R_{min}$, and target value T. The patient navigates between entry fields 60 using the arrow keys on the keypad.

Apparatus 10 uses information derived from insulin time activity profiles to determine the insulin action values. The time activity profiles of insulin are described in several sources, such as Eli Lilly and Company's website http://www.lilly.com/diabetes/ref$_{13}$manual/insulin$_{13}$bck.html. The time activity profiles of insulin are also described in Howey et al. "A Rapidly Absorbed Analogue of Human Insulin", Diabetes, Vol. 43, pp. 396-402, 1994, which is hereby incorporated by reference.

Figure 5:
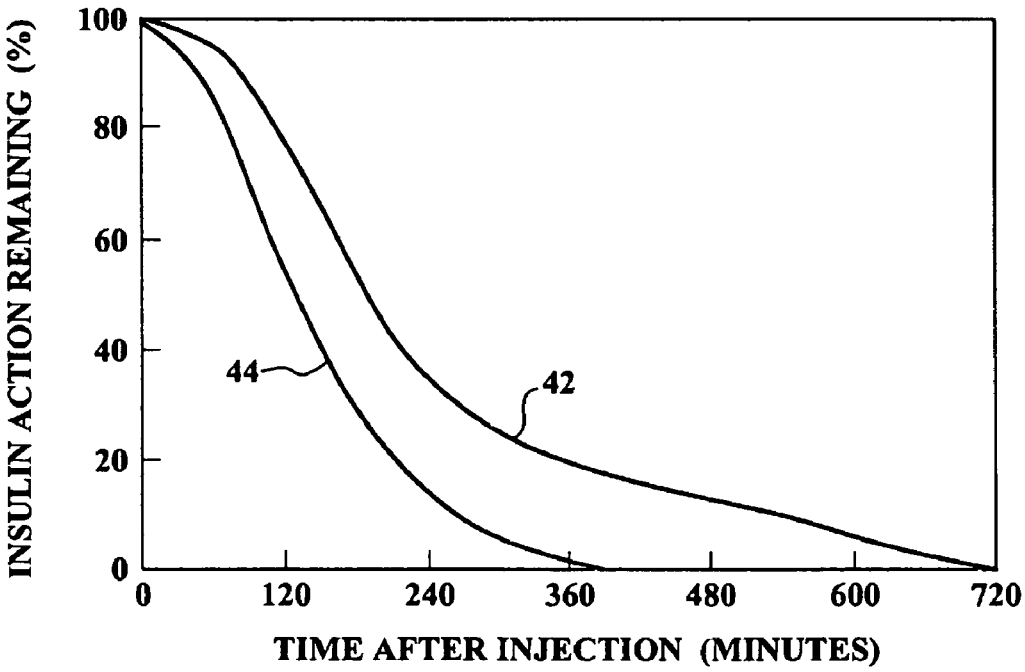
FIG. 5 is a graph illustrating the percent of insulin action remaining from regular and fast acting insulins as a function of time after injection.

FIG. 5 is a graph illustrating the percent of insulin action remaining from doses of regular and lispro insulins as a function of time after injection. The graph includes two insulin action curves derived from data in Howey et al. A first insulin action curve 42 shows the percent of insulin action remaining from a dose of regular insulin as a function of time after injection. A second insulin action curve 44 shows the percent of insulin action remaining from a dose of lispro insulin as a function of time after injection.

An insulin action value is determined from curves 42 or 44 by determining the time after injection, locating the corresponding percentage of insulin action remaining on the appropriate curve, and dividing the percentage by 100 to yield the insulin action value. For example, if the patient injected a dose of lispro and the time after injection equals 150 minutes, then the insulin action value is determined to be 0.40 from curve 44. This indicates that at 150 minutes after injection, the insulin dose has 40% of its full insulin action remaining to lower the patient's blood glucose concentration.

The insulin action curves shown in FIG. 5 are derived from standard patient data. An insulin action curve customized to an individual patient may be generated experimentally by establishing basal homeostasis in the patient and then measuring the effect of a supplemental insulin dose on the patient's blood glucose concentration. After injecting the supplemental insulin dose, the patient's blood glucose is measured frequently over the period of time required for the insulin to be fully absorbed.

The measured blood glucose values are used to generate a curve of the patient's blood glucose concentration as a function of time after injection. The total blood glucose drop resulting from the supplemental insulin dose is determined by subtracting the last blood glucose value from the first blood glucose value. The curve is normalized by subtracting the final blood glucose value from each point on the curve and dividing the result by the total blood glucose drop. Normalizing the curve in this manner yields an insulin action curve individualized to the patient. This experiment is repeated, preferably at varying times of day, to generate a continuous insulin action curve for the patient.

In the preferred embodiment, information for determining insulin action values $F_k(t_d)$ and $F_k(t_j)$ is stored in memory 24 in tabular form. The information may be derived from standard insulin action curves or derived from an insulin action curve individualized to the patient. FIGS. 6A and 6B show a first insulin action Table 1 which is derived from curve 42, the insulin action curve for regular insulin.

FIG. 7 shows a second insulin action Table 2 which is derived from curve 44, the insulin action curve for lispro insulin. Each insulin action table includes a first column containing time points after injection and a second column containing corresponding insulin action values. Microprocessor 22 preferably uses linear interpolation to determine insulin action values $F_k(t_d)$ and $F_k(t_j)$ from the insulin action tables, as will be described in the operation section below.

The operation of the preferred embodiment is illustrated in FIGS. 1-10. Referring to FIG. 2, a preferred method of using the diabetes management system to assist a patient having diabetes mellitus in controlling blood glucose includes the step of storing in memory 24 insulin sensitivity value S, carbohydrate value C, hypoglycemic value H, maximum value $R_{max}$, minimum value $R_{min}$, target blood glucose value T, and the table values for determining remaining insulin action at corresponding times after injection. The values may be entered in apparatus 10 through input/output port 34 or keypad 16. The values stored in memory 24 are preferably selected under the supervision of a healthcare provider, such as the patient's physician.

Insulin sensitivity value S is preferably customized to the patient based upon the patient's measured blood glucose values and insulin dose values, as will be explained in detail below. However, when the patient is first provided with apparatus 10, historical blood glucose values and insulin dose values may not be available. In this case, insulin sensitivity value S is preferably estimated by dividing 1,500 mg/dl by the patient's total daily insulin need. For example, if the patient's total daily insulin need is 30 units, the initial insulin sensitivity value is calculated as 50 mg/dl per unit of insulin.

Specific techniques for establishing carbohydrate value C, hypoglycemic value H, maximum value $R_{max}$, minimum value $R_{min}$, and target blood glucose value T are well known in the art. For example, many physicians prefer a target blood glucose range of 100-150 mg/dl with a target blood glucose value of 120 mg/dl and a hypoglycemic value of 70 mg/dl. Carbohydrate value C is preferably selected in dependence upon the patient's weight. For example, one gram of carbohydrates typically raises blood glucose concentrations by 3 mg/dl, 4 mg/dl, and 5 mg/dl for people who weigh 90 kg, 70 kg, and 45 kg, respectively.

Figure 8A:
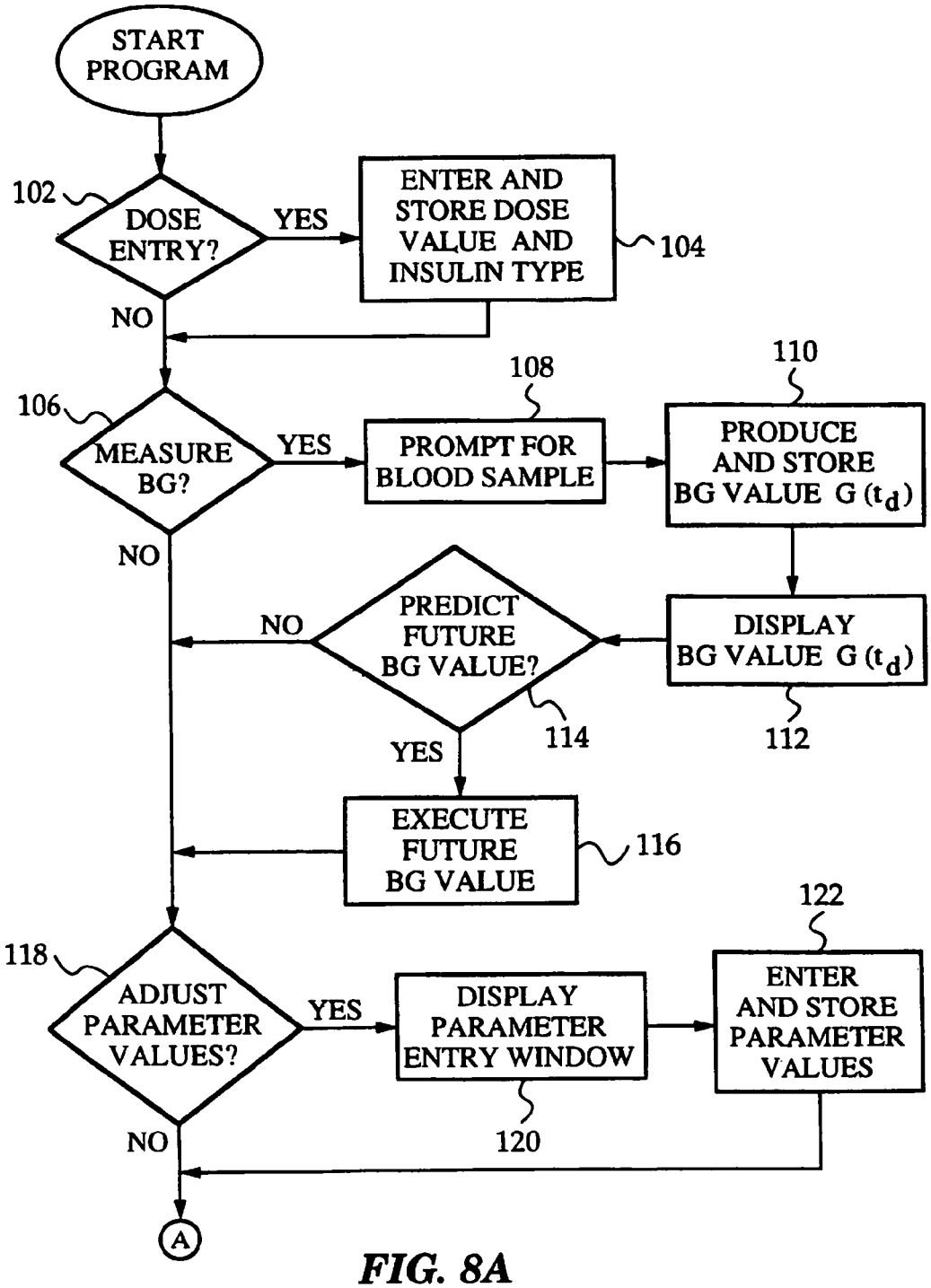
FIG. 8A is a flow chart illustrating steps included in a computer program executed by the apparatus of FIG. 1.
Figure 8B:
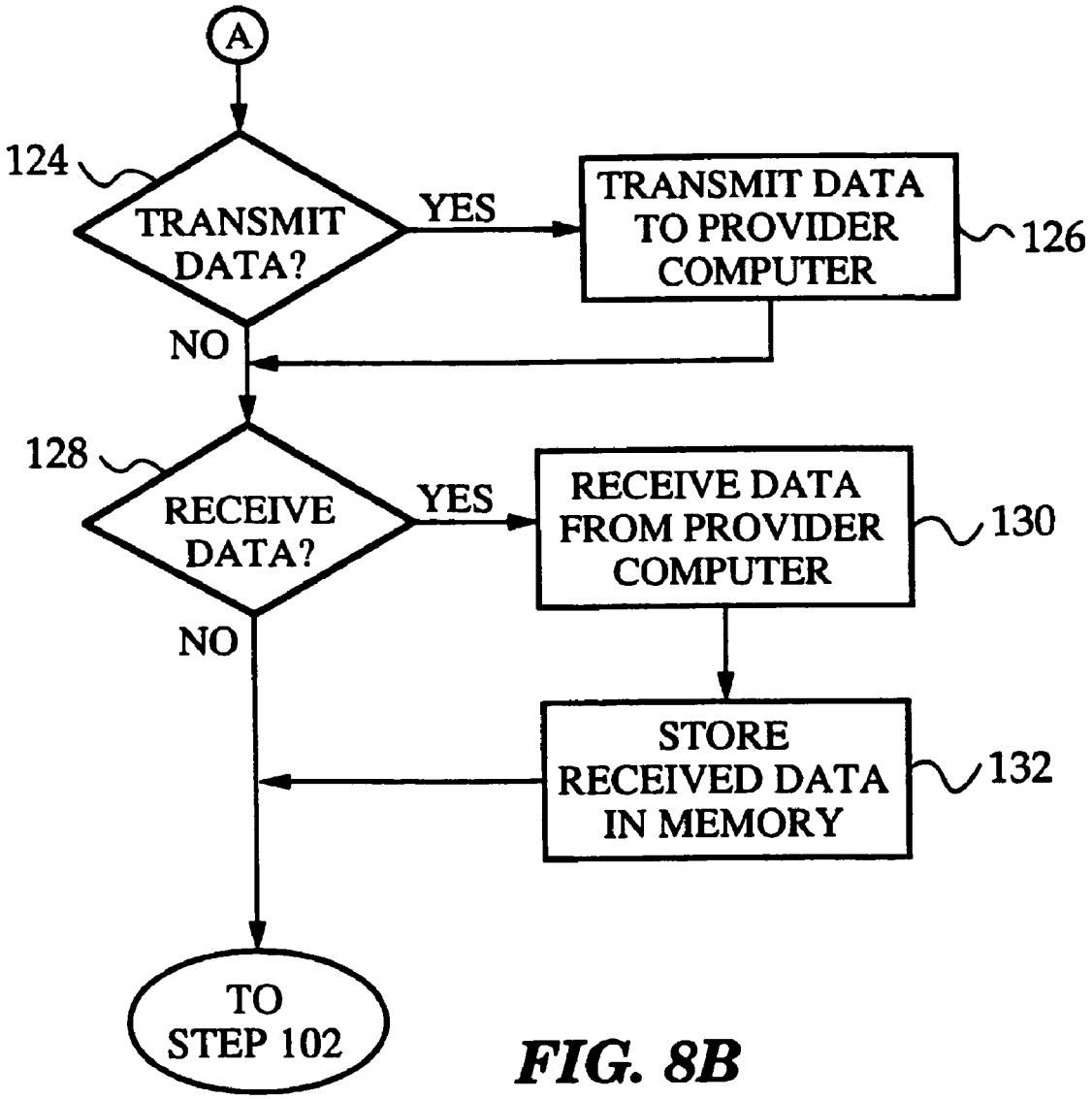
FIG. 8B is a continuation of the flow chart of FIG. 8A.

Apparatus 10 is used by the patient to predict a future blood glucose value and to generate a corrective action when the predicted value lies outside of the patient's target blood glucose range. FIG. 8A is a flow chart illustrating steps included in the computer program executed by microprocessor 22 to perform these functions. FIG. 8B is a continuation of the flow chart of FIG. 8A.

In step 102, microprocessor 22 determines if the patient has selected the "DOSE" option from menu 46. If the patient has not selected the "DOSE" option, microprocessor 22 proceeds to step 106. If the patient has selected the "DOSE" option, microprocessor 22 proceeds to step 104, entering and storing dose value $I_k$ and insulin type $P_k$.

To enter and store dose value $I_k$ and insulin type $P_k$, microprocessor 22 displays the prompt "ENTER DOSE IN UNITS OF INSULIN" on display 14. The patient then enters dose value $I_k$ into microprocessor 22 through keypad 16. The patient is then prompted with "ENTER INSULIN TYPE: PRESS 1 FOR REGULAR OR 2 FOR LISPRO". The patient enters insulin type $P_k$ into microprocessor 22 by pressing the key corresponding to the insulin type injected.

Microprocessor 22 then prompts the patient with "ENTER DATE/TIME OF INJECTION OR PRESS 1 FOR CURRENT DATE/TIME". The patient enters the date and time of injection or selects the current date and time if the dose entry is made immediately after the injection. Microprocessor 22 stores dose value $I_k$ and insulin type $P_k$ in memory 24 with the selected date and time. Following step 104, microprocessor 22 proceeds to step 106.

In step 106, microprocessor 22 determines if the patient has selected the "TEST BG" option from menu 46. If the patient has not selected the "TEST BG" option, microprocessor 22 proceeds to step 118. If the patient has selected the "TEST BG" option, microprocessor 22 prompts the patient to place a blood sample on a blood glucose test strip and to insert the test strip in strip guide 18, step 108.

Glucose meter 28 measures the blood sample and produces blood glucose value $G(t_d)$ from the measurement of the blood sample. In step 110, blood glucose value $G(t_d)$ is entered in microprocessor 22 by glucose meter 28, coded and labeled with the date and time of the measurement, and stored in memory 24. Blood glucose value $G(t_d)$ is also displayed to the patient on display 14 in step 112.

In step 114, microprocessor 22 determines if the patient has selected the "PREDICTION" option from menu 46. If the patient has not selected the "PREDICTION" option, microprocessor 22 proceeds to step 118. If the patient has selected the "PREDICTION" option, microprocessor 22 executes a future blood glucose value program module in step 116. The steps included in the future blood glucose value program module are illustrated in the flow chart of FIGS. 9A and 9B and will be described in detail below. After executing the program module of step 116, microprocessor 22 proceeds to step 118.

In step 118, microprocessor 22 determines if the patient has selected the "VALUES" option from menu 46. If the patient has not selected the "VALUES" option, microprocessor 22 proceeds to step 124. If the patient has selected the "VALUES" option, microprocessor 22 displays on display 14 the parameter value entry window 58, step 120. In step 122, the parameter values are entered in microprocessor 22 through keypad 16 and stored in memory 24. Following step 122, microprocessor 22 proceeds to step 124.

In step 124, microprocessor 22 determines if the patient has selected the "SEND" option from menu 46. If the patient has not selected the "SEND" option, microprocessor 22 proceeds to step 128. If the patient has selected the "SEND" option, microprocessor 22 prompts the patient to connect modem 32 to a telephone line. Microprocessor 22 then transmits the blood glucose values and insulin dose values stored in memory 24 to healthcare provider computer 38 through network 36, step 126. Microprocessor 22 then proceeds to step 128.

In step 128, microprocessor 22 determines if the patient has selected the "RECEIVE" option from menu 46. If the patient has not selected the "RECEIVE" option, microprocessor 22 returns to step 102 and repeats the program steps until apparatus 10 is turned off by the patient. If the patient has selected the "RECEIVE" option, microprocessor 22 prompts the patient to connect modem 32 to a telephone line. In step 130, microprocessor 22 receives data from healthcare provider computer 38 through network 36.

The data preferably includes an adjusted insulin sensitivity value and may optionally include new maximum and minimum values defining the patient's target blood glucose range, a new target blood glucose value, and new insulin action table values for determining remaining insulin action. In step 132, microprocessor 22 stores the received data in memory 24 for use in subsequent calculations. Following step 132, microprocessor 22 returns to step 102 and repeats the program steps until apparatus 10 is turned off by the patient.

Figure 9A:
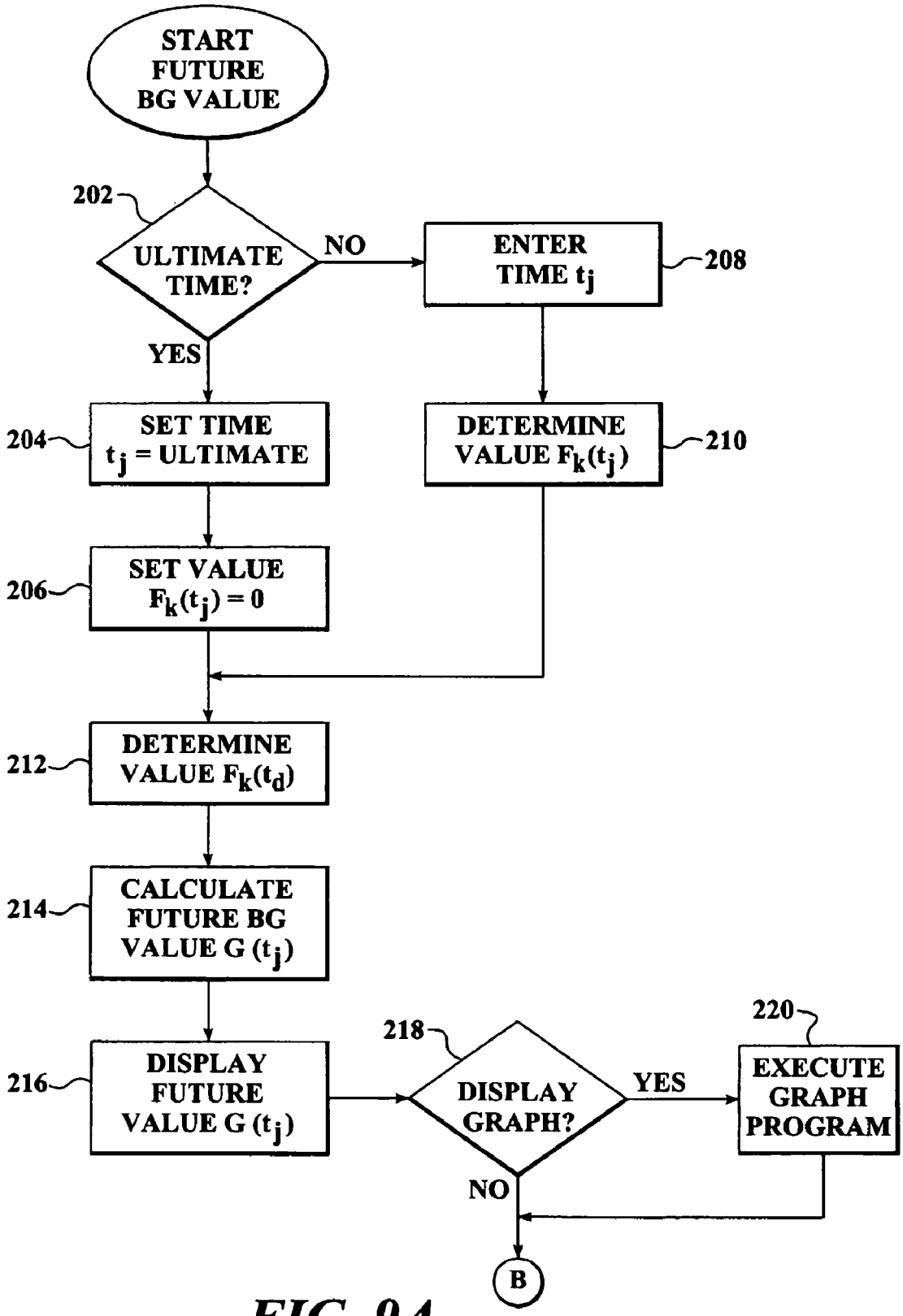
FIG. 9A is a flow chart illustrating steps included in a prediction program module of the computer program of FIGS. 8A and 8B.
Figure 9B:
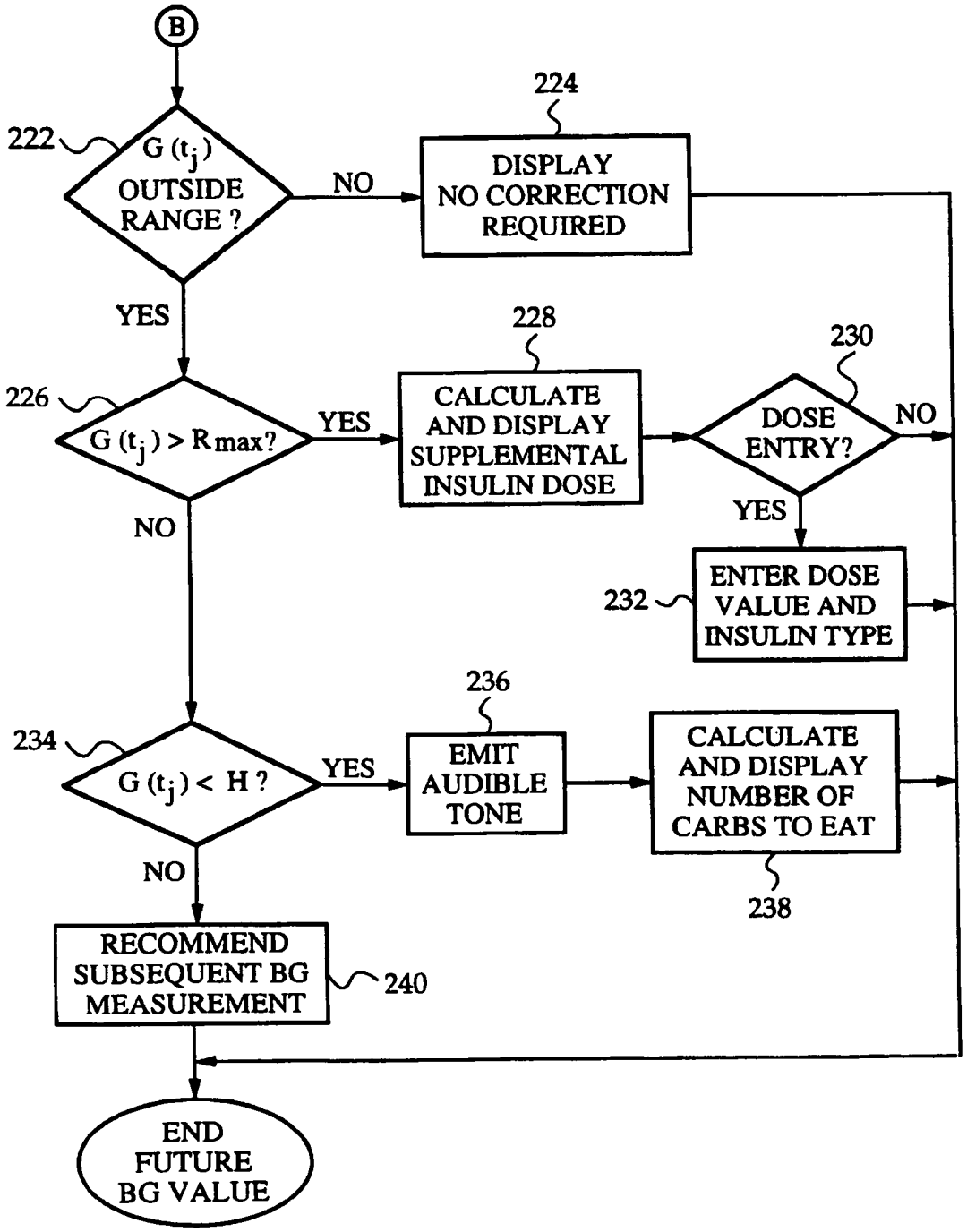
FIG. 9B is a continuation of the flow chart of FIG. 9A.

FIGS. 9A and 9B illustrate the steps included in the future blood glucose value program module of step 116. In step 202, microprocessor 22 determines if the patient wishes to see future blood glucose value $G(t_j)$ predicted for a default ultimate time point by displaying the prompt "USE ULTIMATE TIME IN PREDICTION? YES/NO?". In the preferred embodiment, the ultimate time point is the time point at which the last insulin dose k injected by the patient will be fully absorbed and have no insulin action remaining. In response to a NO input from the patient, microprocessor 22 proceeds to step 208. In response to a YES input from the patient, microprocessor 22 sets time $t_j$ equal to the ultimate time point, step 204.

To set time $t_j$ equal to the ultimate time point, microprocessor 22 retrieves from memory 24 the last insulin dose value $I_k$ and corresponding insulin type $P_k$ entered by the patient. If the insulin type $P_k$ is regular insulin, microprocessor 22 retrieves from Table 1 the time after injection value corresponding to 0.00 insulin action remaining, i.e. 720 minutes. If the insulin type $P_k$ is lispro insulin, microprocessor 22 retrieves from Table 2 the time after injection value corresponding to 0.00 insulin action remaining, i.e. 390 minutes.

Microprocessor 22 adds the retrieved time after injection value to the time of injection stored with the last dose value $I_k$ and sets time $t_j$ equal to the sum. When time $t_j$ is selected to be the ultimate time point, each insulin dose k injected by the patient will have no remaining insulin action at time $t_j$. Accordingly, microprocessor 22 sets insulin action value $F_k(t_j)$ equal to 0 for each dose value $I_k$ stored in memory 24, step 206. Following step 206, microprocessor 22 proceeds to step 212.

If the patient has not selected the ultimate time point for time $t_j$, microprocessor 22 prompts the patient to specify time $t_j$ by displaying "ENTER TIME FOR PREDICTION". The patient then enters time $t_j$ in microprocessor 22 in step 208. In step 210, microprocessor 22 determines insulin action values $F_k(t_j)$ for each dose value $I_k$ stored in memory 24. Microprocessor 22 preferably determines insulin action values $F_k(t_j)$ using linear interpolation.

The insulin action value $F_k(t_j)$ for each dose value $I_k$ is also determined in dependence upon its corresponding insulin type $P_k$. If the insulin type is regular insulin, microprocessor 22 determines the insulin action value $F_k(t_j)$ by interpolating between the values listed in Table 1. If the insulin type is lispro insulin, microprocessor 22 determines the insulin action value $F_k(t_j)$ by interpolating between the values listed in Table 2.

The interpolation is preferably performed as follows. For each dose value $I_k$, microprocessor 22 calculates a time after injection value $X_k$ indicating the time differential between time $t_j$ and the time of injection of dose k. Microprocessor 22 then retrieves four values from the appropriate insulin action table. The four values retrieved are a first time after injection value $X_0$ and its corresponding insulin action value $Y_0$, and a second time after injection value $X_1$ and its corresponding insulin action value $Y_1$.

Value $X_0$ is selected from the appropriate table as the time after injection value which is closest to value $X_k$ without exceeding value $X_k$. Value $X_1$ is selected as the time after injection value in the next row of the table. Microprocessor 22 preferably calculates the insulin action value $F_k(t_j)$ for each dose value according to equation (2A):

$$F_k(t_j) = Y_0 + \frac{(X_k - X_0)(Y_1 - Y_0)}{(X_1 - X_0)}. \tag{2A}$$

For example, if the patient enters a dose value indicating a dose of regular insulin was injected at 12:00 PM and specifies a time $t_j$ of 2:20 PM, microprocessor 22 first calculates time after injection value $X_k$ to be 140 minutes. Microprocessor 22 then retrieves from Table 1 the values $X_0$=135 minutes, $Y_0$=0.70, $X_1$=150 minutes, and $Y_1$=0.64. Microprocessor 22 calculates insulin action value $F_k(t_j)$ for the dose from equation (2A) as:

$$F_k(t_j) = 0.70 + \frac{(140 - 135)(0.64 - 0.70)}{(150 - 135)} = 0.68$$

Microprocessor 22 thus determines that the regular insulin dose injected at 12:00 PM will have 68% of its insulin action remaining at 2:20 PM. Specific techniques for performing linear interpolations in this manner are well known in the art. Further, those skilled in the art will recognize that the insulin action tables could be provided with shorter time intervals between the time points to provide as much precision and accuracy as desired in the interpolation.

In step 212, microprocessor 22 performs a similar linear interpolation to determine the insulin action values $F_k(t_d)$ for each dose value $I_k$ stored in memory 24. The insulin action value $F_k(t_d)$ for each dose value $I_k$ is also determined in dependence upon its corresponding insulin type $P_k$. If the insulin type is regular insulin, microprocessor 22 determines the value $F_k(t_d)$ by interpolating between the values listed in Table 1. If the insulin type is lispro insulin, microprocessor 22 determines the value $F_k(t_d)$ by interpolating between the values listed in Table 2.

For each dose value $I_k$, microprocessor 22 calculates a time after injection value $Z_k$ indicating the time differential between time $t_d$ and the time of injection of dose k. Microprocessor 22 then retrieves from the appropriate insulin action table the first time after injection value $X_0$, the corresponding insulin action value $Y_0$, the second time after injection value $X_1$, and the corresponding insulin action value $Y_1$. Value $X_0$ is selected from the appropriate table as the time after injection value which is closest to value $Z_k$ without exceeding value $Z_k$. Value $X_1$ is selected as the time after injection value in the next row of the table. Microprocessor 22 calculates each insulin action value $F_k(t_d)$ according to equation (2B):

$$F_k(t_d) = Y_0 + \frac{(Z_k - X_0)(Y_1 - Y_0)}{(X_1 - X_0)}. \quad (2B)$$

For example, if the patient enters a dose value indicating a dose of lispro insulin was injected at 8:30 PM and time $t_d$ is 11:00 PM, microprocessor 22 first calculates time after injection value $Z_k$ to be 150 minutes. Microprocessor 22 then retrieves from Table 2 the values $X_0$=150 minutes, $Y_0$=0.40, $X_1$=165 minutes, and $Y_1$=0.32. Microprocessor 22 calculates insulin action value $F_k(t_d)$ for the dose from equation (2B) as:

$$F_k(t_d) = 0.40 + \frac{(150 - 150)(0.32 - 0.40)}{(165 - 150)} = 0.40$$

Microprocessor 22 thus determines that the lispro insulin dose injected at 8:30 PM has 40% of its insulin action remaining at 11:00 PM. In step 214, microprocessor 22 calculates predicted future blood glucose value $G(t_j)$ according to equation (1):

$$G(t_j) = G(t_d) - S\left[\sum_{k=1}^{N} I_k(F_k(t_d) - F_k(t_j))\right] \quad (1)$$

Future blood glucose value $G(t_j)$ is then displayed to the patient on display 14, step 216. In step 218, microprocessor 22 determines if the patient wishes to see graph 48 by displaying the prompt "DISPLAY GRAPH? YES/NO?". In response to a NO input from the patient, microprocessor 22 proceeds to step 222. In response to a YES input from the patient, microprocessor 22 executes a graph program module in step 220. The steps included in the graph program module are illustrated in the flow chart of FIG. 10 and will be described in detail below. After executing the program module of step 220, microprocessor 22 proceeds to step 222.

In step 222, microprocessor 22 compares future blood glucose value $G(t_j)$ to maximum value $R_{max}$ and minimum value $R_{min}$ to determine if future blood glucose value $G(t_j)$ lies outside of the patient's target blood glucose range. If glucose value $G(t_j)$ does not lie outside of the target range, "NO CORRECTIVE ACTION REQUIRED" is displayed to the patient in step 224. Following step 224, the future blood glucose value program module ends.

If glucose value $G(t_j)$ lies outside of the target range, microprocessor 22 determines a corrective action for the patient and recommends the corrective action to the patient on display 14. In step 226, microprocessor 22 determines if glucose value $G(t_j)$ is greater than maximum value $R_{max}$. If glucose value $G(t_j)$ is not greater than maximum value $R_{max}$, microprocessor 22 proceeds to step 234.

If glucose value $G(t_j)$ is greater than maximum value $R_{max}$, microprocessor 22 calculates a supplemental insulin dose D for the patient and displays insulin dose D on display 14, step 228. Microprocessor 22 preferably calculates supplemental insulin dose D in dependence upon insulin sensitivity value S and a difference between future blood glucose value $G(t_j)$ and target blood glucose value T according to equation (3):

$$D=(G(t_j)-T)/S \quad (3).$$

After displaying supplemental insulin dose D, microprocessor 22 determines if the patient wishes to enter a dose value for the supplemental insulin dose by displaying the prompt "SUPPLEMENTAL INSULIN TAKEN? YES/NO?", step 230. In response to a NO input from the patient, the program module ends. In response to a YES input, microprocessor 22 proceeds to step 232, entering and storing the dose value and insulin type of supplemental insulin dose D. Step 232 is analogous to step 104 previously described with reference to FIG. 7A. Following step 232, the program module ends.

In step 234, microprocessor 22 determines if glucose value $G(t_j)$ is less than hypoglycemic value H. If future blood glucose value $G(t_j)$ is not less than hypoglycemic value H, microprocessor 22 proceeds to step 240. If glucose value $G(t_j)$ lies below hypoglycemic value H, microprocessor 22 audibly alerts the patient by causing speaker 54 to emit audible tones, step 236. This alerts the patient that he or she is likely to develop hypoglycemia unless a carbohydrate supplement is taken.

In step 238, microprocessor 22 calculates a number B of grams of carbohydrates to be consumed by the patient and displays a recommendation to consume number of grams B, step 238. Following step 238, the program module ends. Microprocessor 22 preferably calculates number of grams B in dependence upon carbohydrate value C and the difference between future blood glucose value $G(t_j)$ and target blood glucose value T according to equation (4):

$$B=(T-G(t_j))/C \quad (4).$$

If future blood glucose value $G(t_j)$ is not less than hypoglycemic value H, then glucose value $G(t_j)$ lies in a range between hypoglycemic value H and minimum value $R_{min}$.

In this case, microprocessor 22 displays to the patient "POSSIBLE FUTURE HYPOGLYCEMIA: RECOMMEND SUBSEQUENT GLUCOSE MEASUREMENT IN 1.5 HOURS", step 240. Following step 240, the program module ends. Because the patient's blood glucose concentration may rebound, it is presently preferred not to recommend a carbohydrate supplement unless future blood glucose value $G(t_j)$ is below hypoglycemic value H.

Figure 10:
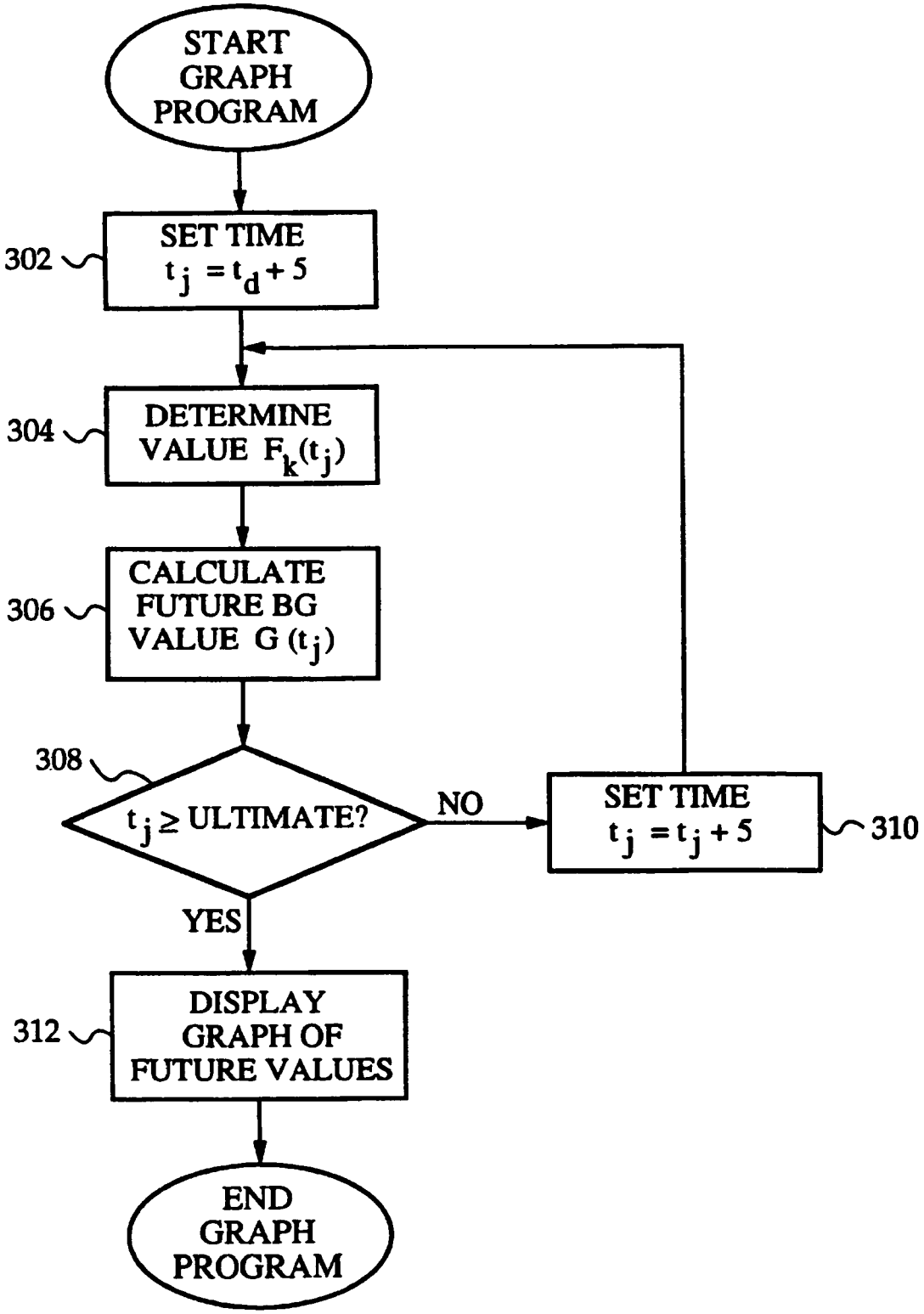
FIG. 10 is a flow chart illustrating steps included in a graph program module of the computer program of FIGS. 8A and 8B.

FIG. 10 is a flow chart illustrating the steps included in the graph program module of step 220. In steps 302-310, microprocessor 22 generates a plurality of predicted future blood glucose values for various time points between time $t_d$ and time $t_j$. The future blood glucose values are used to generate blood glucose value curve 50 of graph 48. In the preferred embodiment, the future blood glucose values are calculated for time points which increase from time $t_d$ to time $t_j$ in five minute increments. It is obvious that the time increments may be varied as desired in alternative embodiments.

In step 302, microprocessor 22 sets time $t_j$ equal to time $t_d$ plus five minutes. In step 304, microprocessor 22 determines insulin action values $F_k(t_j)$ for each dose value $I_k$ stored in memory 24. Step 304 is analogous to step 210 previously described with reference to FIG. 9A. In step 306, microprocessor 22 calculates future blood glucose value $G(t_j)$. Step 306 is analogous to step 214 previously described with reference to FIG. 9A.

In step 308, microprocessor 22 determines if time $t_j$ is greater than or equal to the ultimate time point at which the last insulin dose k injected by the patient will have no insulin action remaining. If time $t_j$ is not greater than or equal to the ultimate time point, microprocessor 22 sets time $t_j$ equal to time $t_j$ plus five minutes, step 310. Microprocessor 22 then repeats steps 304-308 to calculate a subsequent future blood glucose value.

If time $t_j$ is greater than or equal to the ultimate time point, microprocessor 22 generates blood glucose value curve 50 from the calculated future blood glucose values and displays graph 48 on display 14, step 312. Following step 312, the graph program module ends. As shown in FIG. 1, graph 48 includes line 52 indicating the patient's hypoglycemic threshold and line 53 indicating the patient's hyperglycemic threshold. Lines 52 and 53 enable the patient to determine the time point at which he or she is predicted to develop hypoglycemia and hyperglycemia, respectively.

The diabetes management system of the present invention provides a significant improvement over conventional diabetes management systems by alerting the patient to the possible development of hypoglycemia or hyperglycemia between meals, thereby allowing the patient to take early corrective action. Conventional management systems are unable to account for the insulin action remaining from previous insulin doses and therefore restrict insulin supplements to pre-meal times. Thus, in using these conventional systems, the patient must wait until the next meal time to correct hyperglycemia, and may develop hypoglycemia without warning.

The following is an illustrative example of how apparatus 10 assists a patient in preventing hyperglycemia between meals. The example assumes the patient has an insulin sensitivity value of 40 mg/dl per unit, a target blood glucose range of 100 mg/dl-150 mg/dl, a target blood glucose value of 120 mg/dl, a hypoglycemic value of 70 mg/dl, and a carbohydrate value of 4 mg/dl per gram.

In the example, the patient eats a late dinner at 8:40 PM. Before eating, the patient estimates that the meal requires 15 units of bolus insulin and injects 15 units of lispro at 8:30 PM. The patient records the dose value, dose type, and time of injection in apparatus 10. At bedtime, 11:00 PM, the patient uses apparatus 10 to measure his or her blood glucose value. Apparatus 10 produces and displays to the patient a current blood glucose value of 480 mg/dl. The patient then requests apparatus 10 to predict a future blood glucose value at the ultimate time point.

Microprocessor 22 retrieves from memory 24 the dose value and corresponding insulin type of the dose injected by the patient at 8:30 PM. Microprocessor 22 calculates time after injection value $Z_k$ to be 150 minutes. Microprocessor 22 then retrieves from Table 2 the values $X_0$=150 minutes, $Y_0$=0.40, $X_1$=165 minutes, and $Y_1$=0.32. Microprocessor 22 calculates insulin action value $F_k(t_d)$ from equation (2B) as:

$$F_k(t_d) = 0.40 + \frac{(150-150)(0.32-0.40)}{(165-150)} = 0.40.$$

Microprocessor 22 thus determines that the lispro insulin dose injected at 8:30 PM has 40% of its insulin action remaining at 11:00 PM. Microprocessor 22 also sets insulin action value $F_k(t_j)$ equal to 0.0 for each dose value stored in memory 24. For simplicity of understanding, the example assumes that only the dose injected at 8:30 PM has remaining insulin action. Microprocessor 22 then calculates the predicted blood glucose value at 3:00 AM according to equation (1) as:

$$G(t_j)=480-40(15\times.40)=240 \text{ mg/dl}.$$

This indicates that the patient can expect an ultimate blood glucose value of 240 mg/dl when the insulin dose has been completely absorbed. The predicted value of 240 mg/dl is greater than the patient's maximum value of 150 mg/dl, so microprocessor 22 calculates a supplemental insulin dose for the patient and displays the recommended supplement on display 14. The supplemental dose D is calculated from equation (3) as:

$$D=(240-120)/40=3 \text{ units of supplemental insulin}.$$

The patient takes the supplemental insulin dose and records the dose value in apparatus 10. From taking the supplemental insulin dose, the patient obtains eight hours of normal blood glucose in place of hyperglycemia. An adjusted insulin sensitivity may also be determined from the dose values and measured blood glucose values recorded in apparatus 10 as follows. The next morning, the patient measures his or her pre-breakfast blood glucose value using apparatus 10. The patient then transmits the recorded dose values and blood glucose values measured at bedtime and before breakfast to healthcare provider computer 38.

An adjusted insulin sensitivity value is calculated in healthcare provider computer 38 by subtracting the pre-breakfast blood glucose value from the bedtime blood glucose value. The result is divided by the total number of units of insulin which had remaining insulin action at bedtime. The number of units of insulin having remaining insulin action at bedtime is equal to the total number of units of the supplemental insulin dose plus the fraction of any previously injected insulin doses having remaining action.

An illustrative example will now be given using the same values presented above, where the patient's bedtime blood glucose value equals 480 mg/dl, the supplemental insulin dose value equals 3 units, and the fraction of insulin action remaining from a previous 15 unit insulin dose is 0.40. The present example further assumes a pre-breakfast blood glucose value of 138 mg/dl measured the following morning. The adjusted sensitivity value is calculated as:

$$S=(480-138)/(3+(15\times0.40))=38 \text{ mg/dl per unit}.$$

The insulin sensitivity value S is preferably updated over time as a moving average of the individually calculated sensitivity values.

A second example illustrates how apparatus 10 assists a patient in preventing hypoglycemia. The second example assumes the same values presented in the first example except that the patient's blood glucose value at 11:00 PM is now assumed to be 280 mg/dl. Microprocessor 22 calculates the predicted glucose value at 3:00 AM from equation (1) as:

$$G(t_j)=280-40(15\times0.40)=40 \text{ mg/dl}.$$

The predicted value of 40 mg/dl is less than the patient's hypoglycemic value of 70 mg/dl. Accordingly, microprocessor 22 calculates a carbohydrate supplement and displays the number of grams of carbohydrates to be consumed by the patient. The number of grams of carbohydrates is calculated from equation (4) as:

$$B=(120 \text{ mg/dl}-40 \text{ mg/dl})/4=20 \text{ grams}.$$

The patient consumes the carbohydrate supplement and successfully avoids hypoglycemia.

SUMMARY, RAMIFICATIONS, AND SCOPE

Although the above description contains many specificities, these should not be construed as limitations on the scope of the invention but merely as illustrations of the presently preferred embodiment. Many other embodiments of the invention are possible. For example, the system of the invention may be implemented in many different hardware configurations. It is presently preferred to provide the patient with a small, portable apparatus to facilitate use of the apparatus throughout the day. However, in alternative embodiments, the apparatus may comprise a personal computer, a multi-media processor connected to a television, or any other electronic device capable of performing the functions described.

Additionally, the system is not limited to establishing a communication link between the apparatus and healthcare provider computer through a telephone line or data connection cord. Those skilled in the art will recognize that the apparatus may be placed in communication with the healthcare provider computer through a computer network, a wireless communication network, or a data storage card, such as a smart card, exchanged between the physician and patient. Specific techniques for establishing communication links between a physician and a remotely located patient are well known in the art.

The insulin sensitivity values and insulin action values for determining remaining insulin action may differ in alternative embodiments. The values shown in the preferred embodiment are exemplary of one possible embodiment of the invention and are not intended to limit its scope. Further, the insulin action values may be derived from standard data or derived from the blood glucose values and insulin dose values of an individual patient. The insulin action values may be further customized to the individual patient in dependence upon the patient's preferred mode of insulin administration, e.g. syringe injections into the thigh, gut, or arm, insulin pump administrations, or inhalation.

Further, the insulin action values need not be stored in tabular form. In an alternative embodiment, the apparatus stores first and second mathematical equations derived from the insulin action curves. The first equation expresses remaining insulin action as a function of time after injection of a dose of regular insulin. The second equation expresses remaining insulin action as a function of time after injection of a dose of lispro insulin. In this embodiment, the apparatus determines an insulin action value by determining the time after injection and calculating the insulin action value using the equation corresponding to the type of insulin injected.

The preferred embodiment includes a patient-operated apparatus and a healthcare provider computer in communication with the apparatus. This configuration of system components is presently preferred for ease of setting, storing, and adjusting the target blood glucose value and insulin sensitivity value of the patient under the supervision of a healthcare provider. However, those skilled in the art will recognize that the apparatus itself may also be programmed to adjust the patient's insulin sensitivity value based upon the stored blood glucose values and insulin dose values, eliminating the need for the healthcare provider computer if physician review is deemed unnecessary.

It is presently preferred to include a blood glucose meter in the apparatus for automated entry of blood glucose values. However, the apparatus need not include a blood glucose meter. In one alternative embodiment, the blood glucose meter is separate from the apparatus and the patient manually enters measured blood glucose values into the apparatus through the keypad. In another embodiment, the blood glucose meter is connectable to the apparatus through a serial input/output port for automated uploading of the blood glucose values. Similarly, in embodiments of the apparatus which include a modem, the modem need not be built into the apparatus. In alternative embodiments, the apparatus may be adapted to receive a separate modem card, as is well known in the art.

Moreover, the apparatus is not limited to storing patient data relating only to blood glucose and insulin dose values. In alternative embodiments, the apparatus also stores guidelines for diet, exercise, and other therapy parameters. Further, the apparatus may be programmed to prompt a patient for data relating to the therapy parameters and to display recommended guidelines to the patient.

Additionally, the invention may also be implemented as a simulation system for educating and training patients in blood glucose control. In the simulation embodiment, the insulin dose values are representative of simulated insulin doses and the blood glucose values are representative of simulated blood glucose concentrations. The patient enters various insulin dose values and blood glucose values in the simulation system to learn their effect on his or her future blood glucose concentration.

Therefore, the scope of the invention should be determined not by the examples given but by the appended claims and their legal equivalents.

What is claimed is:

1. An apparatus for assisting a patient having diabetes mellitus in controlling blood glucose, said apparatus comprising:

a) an input means for entering a blood glucose value $G(t_d)$ representative of a blood glucose concentration of the patient at time $t_d$ and for entering an insulin dose value $I_k$ representative of an insulin dose administered to the patient prior to time $t_d$;

b) a memory means for storing an insulin sensitivity value representative of an insulin sensitivity of the patient and for storing information for determining an insulin action value $F_k(2^d)$ representative of a fraction of insulin action remaining at time $t_d$ from said insulin dose;

c) a processor connected to said input means and said memory means for determining said insulin action value $F_k(t_d)$ and for determining a future blood glucose value $G(t_j)$ representative of an expected blood glucose concentration of the patient at time $t_j$, wherein said processor determines said future blood glucose value $G(t_j)$ in dependence upon said blood glucose value $G(t_d)$, said insulin dose value $I_k$, said insulin sensitivity value, and said insulin action value $F_k(t_d)$;

d) an interpolation formula to calculate the insulin action value $F_k(t_d)$ programmed into the processor, the formula to calculate the insulin action value comprising $$F_k(t_d)=Y_0+((Z_k-X_0)(Y_1-Y_0)/(X_1-X_0))$$

wherein $X_0$ represents an initial insulin dose, $Y_0$ represents an insulin action value at initial dose $X_0$, $X_1$ represents a following insulin dose, $Y_1$ represents an insulin action value at following insulin dose $X_1$, and $Z_k$ represents time after injection of insulin dose $I_k$ at time $t_d$;

e) a formula to calculate the future blood glucose value $G(t_j)$ programmed into the processor, the formula to calculate the food glucose value comprising:

$$G(t_j) = G(t_d) - S\left[\sum_{k=1}^{N} I_k F_k(t_d) - F_k(t_j)\right]$$

wherein S represents insulin sensitivity values, $I_k$ represents insulin dose values administered prior to time $t_d$, and $F_k(t_j)$ represents insulin action values at time $(t_j)$, k=1 represents a single insulin bolus dose and a supplemental insulin bolus dose, and N represents the total number of insulin bolus doses and supplemental insulin bolus doses; and f) a display means connected to said processor for displaying said future blood glucose value $G(t_j)$, thereby enabling the patient to take timely corrective action to prevent hypoglycemia or hyperglycemia.

2. The apparatus of claim 1, wherein said memory means includes means for storing maximum and minimum values defining a target blood glucose range of the patient, said processor includes means for determining if said future blood glucose value $G(t_j)$ lies outside of said target range and means for determining said corrective action for the patient when said future blood glucose value $G(t_j)$ lies outside of said target range, and said display means includes means for recommending said corrective action to the patient.

3. The apparatus of claim 2, wherein said memory means further includes means for storing a target blood glucose value of the patient, said corrective action comprises an administration of a supplemental insulin dose, and said processor further comprises means for determining said supplemental insulin dose in dependence upon said insulin sensitivity value and a difference between said future blood glucose value $G(t_j)$ and said target blood glucose value.

4. The apparatus of claim 2, wherein said memory means further includes means for storing a target blood glucose value of the patient, said corrective action comprises a consumption of a number of grams of carbohydrates, and said processor further comprises means for determining said number of grams in dependence upon a difference between said future blood glucose value $G(t_j)$ and said target blood glucose value.

5. The apparatus of claim 1, wherein said memory means further includes means for storing a hypoglycemic value indicative of a hypoglycemic threshold of the patient, said processor includes means for determining if said future blood glucose value $G(t_j)$ lies below said hypoglycemic value, and said apparatus further comprises audio means connected to aid processor for audibly alerting the patient when said future blood glucose value $G(t_j)$ lies below said hypoglycemic value.

6. The apparatus of claim 1, wherein said input means comprises a blood glucose measuring means for measuring a blood sample of the patient and for producing said blood glucose value $G(t_d)$ from a measurement of said blood sample.

7. The apparatus of claim 1, wherein said insulin dose has an insulin type, said input means includes means for entering said insulin type, and said processor includes means for determining said insulin action value $F_k(t_d)$ in dependence upon said insulin type.

8. The apparatus of claim 7, wherein said insulin type is selected from the group consisting of regular insulin and lispro insulin.

9. The apparatus of claim 1, wherein said processor includes means for determining an insulin action value $F_k(t_j)$ representative of a fraction of insulin action remaining at time $t_j$ from said insulin dose and means for determining said future blood glucose $G(t_j)$ in further dependence upon said insulin action value $F_k(t_j)$.

10. The apparatus of claim 1, wherein said processor includes means for determining an ultimate time point at which said insulin dose will have no insulin action remaining and means for setting time $t_j$ equal to said ultimate time point.

11. The apparatus of claim 1, wherein said processor includes means for determining a plurality of future blood glucose values representative of a corresponding plurality of expected blood glucose concentrations of the patient, and wherein said display means includes means for displaying said future blood glucose values in graphical form.

12. The apparatus of claim 1, further comprising a communication means connected to said processor for establishing a communication link between said apparatus and a healthcare provider computer and for transmitting and receiving data therebetween.

13. The apparatus of claim 12, wherein said communication means comprises a modem means for establishing said communication link through a communication network.

14. The apparatus of claim 12, wherein said communication means comprises an input/output port for establishing said communication link through a connection cord.

15. A system for assisting a patient having diabetes mellitus in controlling blood glucose, said system comprising:

a) an input means for entering a blood glucose value $G(t_d)$ representative of a blood glucose concentration of the patient at time $t_d$ and for entering an insulin dose value $I_k$ representative of an insulin dose administered to the patient prior to time $t_d$;

b) a memory means for storing maximum and minimum values defining a target blood glucose range of the patient, an insulin sensitivity value representative of an insulin sensitivity of the patient, and information for determining an insulin action value $F_k(t_d)$ representative of a fraction of insulin action remaining at time $t_d$ from said insulin dose;

c) a processor connected to said input means and said memory means for determining said insulin action value $F_k(t_d)$, for determining a future blood glucose value $G(t_j)$ representative of an expected blood glucose concentration of the patient at time $t_j$, and for determining a corrective action for the patient when said future blood glucose value $G(t_j)$ lies outside of said target range, wherein said processor determines said future blood glucose value $G(t_j)$ in dependence upon said blood glucose value $G(t_d)$, said insulin dose value, said insulin sensitivity value, and said insulin action value $F_k(t_d)$; and d) an interpolation formula to calculate the insulin action value $F_k(t_d)$ programmed into the processor, the formula to calculate the insulin action value comprising:

$$F_k(t_d)=Y_0+((Z_k-X_0)(Y_1-Y_0)/(X_1-X_0))$$

wherein $X_0$ represents an initial insulin dose, $Y_0$ represents an insulin action value at initial dose $X_0$, $X_1$ represents a following insulin dose, $Y_1$, represents an insulin action value at following insulin dose $X_1$, and $Z_k$ represents time after injection of insulin dose $I_k$ at time $t_d$;

e) a formula to calculate the future blood glucose value $G(t_j)$ programmed into the processor, the formula to calculate the food glucose value comprising.

$$G(t_j) = G(t_d) - S\left[\sum_{k=1}^{N} I_k F_k(t_d) - F_k(t_j)\right]$$

wherein S represents insulin sensitivity values, $I_k$ represents insulin dose values administered prior to time $t_d$, and $F_k(t_j)$ represents insulin action values at time $(t_j)$, k=1 represents a single insulin bolus dose and a supplemental insulin bolus dose, and N represents the total number of insulin bolus doses and supplemental insulin bolus doses; and f) a display means connected to said processor for recommending said corrective action to the patient.

16. The system of claim 15, wherein said memory means further includes means for storing a target blood glucose value of the patient, said corrective action comprises an administration of a supplemental insulin dose, and said processor further comprises means for determining said supplemental insulin dose in dependence upon said insulin sensitivity value and a difference between said future blood glucose value $G(t_j)$ and said target blood glucose value.

17. The system of claim 15, wherein said memory means further includes means for storing a target blood glucose value of the patient, said corrective action comprises a consumption of a number of grams of carbohydrates, and said processor further comprises means for determining said number of grams in dependence upon a difference between said future blood glucose value $G(t_j)$ and said target blood glucose value.

18. The system of claim 15, wherein said memory means further includes means for storing a hypoglycemic value indicative of a hypoglycemic threshold of the patient, said processor includes means for determining if said future blood glucose $G(t_j)$ lies below said hypoglycemic value, and said system further comprises audio means connected to said processor for audibly alerting the patient when said future blood glucose value $G(t_j)$ lies below said hypoglycemic value.

19. The system of claim 15, wherein said input means comprises a blood glucose measuring means for measuring a blood sample of the patient and for producing said blood glucose value $G(t_d)$ from a measurement of said blood sample.

20. The system of claim 15, wherein said insulin dose has an insulin type, said input means includes means for entering said insulin type, and said processor includes means for determining said insulin action value $F_k(t_d)$ in dependence upon said insulin type.

21. The system of claim 20, wherein said insulin type is selected from the group consisting of regular insulin and lispro insulin.

22. The system of claim 15, wherein said processor includes means for determining an insulin action value $F_k(t_j)$ representative of a fraction of insulin action remaining at time $t_j$ from said insulin dose and means for determining said future blood glucose value $G(t_j)$ in further dependence upon said insulin action value $F_k(t_j)$.

23. The system of claim 15, wherein said processor includes means for determining an ultimate time point at which said insulin dose will have no insulin action remaining and means for setting time $t_j$ equal to said ultimate time point.

24. The system of claim 15, wherein said processor includes means for determining a plurality of future blood glucose values representative of a corresponding plurality of expected blood glucose concentrations of the patient, and wherein said display means includes means for displaying said future blood glucose values in graphical form.

25. The system of claim 15, wherein said input means includes means for entering a plurality of blood glucose values and a plurality of insulin dose values, and said system further comprises a computing means in communication with said processor for receiving said blood glucose values and said insulin dose values and for calculating from said blood glucose values and said insulin dose values an adjusted insulin sensitivity value.

26. The system of claim 25, wherein said input means, said memory means, said processor, and said display means are included in a patient-operated apparatus, said computing means comprises a healthcare provider computer, and said apparatus includes a communication means connected to said processor for establishing a communication link between said apparatus and said healthcare provider computer.

27. The system of claim 26, wherein said communication means comprises a modem means for establishing said communication link through a communication network.

28. The system of claim 26, wherein said communication means comprises an input/output port for establishing said communication link through a connection cord.

29. A method for assisting a patient having diabetes mellitus in controlling blood glucose, said method comprising the following steps:

a) providing the patient with an apparatus for determining a future blood glucose value $G(t_j)$ representative of an expected blood glucose concentration of the patient at time $t_j$, wherein said apparatus comprises a memory, an input means for entering a blood glucose value $G(t_d)$ representative of a blood glucose concentration of the patient at time $t_d$ and for entering an insulin dose value representative of an insulin dose administered to the patient prior to time $t_d$, a display, and a processor connected to said memory, said input means, and said display;

b) storing in said memory an insulin sensitivity value representative of an insulin sensitivity of the patient;

c) storing in said memory information for determining an insulin action value $F_k(t_d)$ representative of a fraction of insulin action remaining at time $t_d$ from said insulin dose;

d) entering in said processor said insulin dose value and said blood glucose value $G(t_d)$;

e) determining in said processor said insulin action value $F_k(t_d)$ by programming the processor to execute an interpolation formula to calculate the insulin action value $F_k(t_d)$ programmed into the processor, the formula to calculate the insulin action value comprising:

$$F_k(t_d)=Y_0+((Z_k-X_0)(Y_1-Y_0)/(X_1-X_0))$$

wherein $X_0$ represents an initial insulin dose, $Y_0$ represents an insulin action value at initial dose $X_0$, $X_1$ represents a following insulin dose, $Y_1$ represents an insulin action value at following insulin dose $X_1$, and $Z_k$ represents time after injection of insulin dose $I_k$ at time $t_d$;

f) determining in said processor said future blood glucose value $G(t_j)$ in dependence upon said blood glucose value $G(t_d)$, said insulin dose value, said insulin sensitivity value, and said insulin action value $F_k(t_d)$ by programming the processor to execute a formula to calculate the future blood glucose value $G(t_j)$ programmed into the processor, the formula to calculate the food glucose value comprising:

$$G(t_j) = G(t_d) - S\left[\sum_{k=1}^{N} I_k F_k(t_d) - F_k(t_j)\right]$$

wherein S represents insulin sensitivity values, $I_k$ represents insulin dose values administered prior to time $t_d$, and $F_k(t_j)$ represents insulin action values at time $(t_j)$, k=1 represents a single insulin bolus dose and a supplemental insulin bolus dose, and N represents the total number of insulin bolus doses and supplemental insulin bolus doses; and g) displaying said future blood glucose value $G(t_j)$ on said display, thereby enabling the patient to take timely corrective action to prevent hypoglycemia or hyperglycemia.

30. The method of claim 29, further comprising the step of determining in said processor an insulin action value $F_k(t_j)$ representative of a fraction of insulin action remaining at time $t_j$, from said insulin dose, and wherein said future blood glucose value $G(t_j)$ is determined in further dependence upon said insulin action value $F_k(t_j)$.

31. The method of claim 29, wherein the step of determining said future blood glucose value $G(t_j)$ is preceded by the steps of determining in said processor an ultimate time point at which said insulin dose will have no insulin action remaining and setting time $t_j$ equal to said ultimate time point.

32. The method of claim 29, further comprising the steps of determining in said processor a plurality of future blood glucose values representative of a corresponding plurality of expected blood glucose concentrations of the patient and displaying said future blood glucose values in graphical form on said display.

33. The method of claim 29, further comprising the steps of storing in said memory maximum and minimum values defining a target blood glucose range of the patient, determining in said processor if said future blood glucose value $G(t_j)$ lies outside of said target range, determining in said processor said corrective action for the patient when said future blood glucose value $G(t_j)$ lies outside of said target range, and recommending said corrective action on said display.

34. The method of claim 33, wherein said corrective action comprises an administration of a supplemental insulin dose, and said method further comprises the steps of storing in said memory a target blood glucose value of the patient and determining in said processor said supplemental insulin dose in dependence upon said insulin sensitivity value and a difference between said future blood glucose value $G(t_j)$ and said target blood glucose value.

35. The method of claim 33, wherein said corrective action comprises a consumption of a number of grams of carbohydrates, and said method further comprises the steps of storing in said memory a target blood glucose value of the patient and determining in said processor said number of grams in dependence upon a difference between said future blood glucose value $G(t_j)$.

36. The method of claim 29, further comprising the steps of storing in said memory a hypoglycemic value indicative of a hypoglycemic threshold of the patient, determining in said processor if said future blood glucose value $G(t_j)$ lies below said hypoglycemic value, and audibly alerting the patient when said future blood glucose value $G(t_j)$ lies below said hypoglycemic value.

37. The method of claim 29, wherein said input means comprises a blood glucose meter and the step of entering said blood glucose value $G(t_d)$ comprises the steps of measuring a blood sample of the patient with said glucose meter and producing said blood glucose value $G(t_d)$ from a measurement of said blood sample.

38. The method of claim 29, wherein said insulin dose has an insulin type, said method further comprises the step of entering said insulin type in said processor, and said insulin action value $F_k(t_d)$ is determined in dependence upon said insulin type.

39. The method of claim 38, wherein said insulin type is selected from the group consisting of regular insulin and lispro insulin.

40. A method for assisting a patient having diabetes mellitus in controlling blood glucose, said method comprising the following steps:

a) providing the patient with an apparatus for determining a future blood glucose value $G(t_j)$ representative of an expected blood glucose concentration of the patient at time $t_j$, wherein said apparatus comprises a memory, an input means for entering a blood glucose value $G(t_d)$ representative of a blood glucose concentration of the patient at time $t_d$ and for entering an insulin dose value representative of an insulin dose administered to the patient prior to time $t_d$, a display, an a processor connected to said memory, said input means, and said display;

b) storing in said memory an insulin sensitivity value representative of an insulin sensitivity of the patient, information for determining an insulin action value $F_k(t_d)$ representative of a fraction of insulin action remaining at time $t_d$ from said insulin dose, and maximum and minimum values defining a target blood glucose range of the patient;

c) entering in said processor said insulin dose value and said blood glucose value $G(t_d)$;

d) determining in said processor said insulin action value $F_k(t_d)$ by programming the processor to execute an interpolation formula to calculate the insulin action value $F_k(t_d)$ as stated in the formula to calculate the insulin action value comprising:

$$F_k(t_d)=Y_{0+}((Z_k-X_0)(Y_1-Y_0)/(X_1-X_0))$$

wherein $X_0$ represents an initial insulin dose, $Y_0$ represents an insulin action value at initial dose $X_0$, $X_1$ represents a following insulin dose, $Y_1$ represents an insulin action value at following insulin dose $X_1$, and $Z_k$ represents time after injection of insulin dose $I_k$ at time $t_d$;

e) determining in said processor said future blood glucose value $G(t_j)$ by programming the processor to execute a formula to calculate the future blood glucose value $G(t_j)$ using the formula to calculate the food glucose value comprising:

$$G(t_j) = G(t_d) - S\left[\sum_{k=1}^{N} I_k F_k(t_d) - F_k(t_j)\right]$$

wherein S represents insulin sensitivity values, $I_k$ represents insulin dose values administered prior to time $t_d$, and $F_k(t_j)$ represents insulin action values at time $(t_j)$, k=1 represents a single insulin bolus dose and a supplemental insulin bolus dose, and N represents the total number of insulin bolus doses and supplemental insulin bolus doses, and in dependence upon said blood glucose value $G(t_d)$, said insulin dose value, said insulin sensitivity value, and said insulin action value $F_k(t_d)$;

f) determining in said processor if said future blood glucose value $G(t_j)$ lies outside of said target range;

g) determining in said processor a corrective action for the patient when said future blood glucose value $G(t_j)$ lies outside of said target range; and h) recommending said corrective action to the patient on said display.

41. The method of claim 40, further comprising the step of determining in said processor an insulin action value $F_k(t_j)$ representative of a fraction of insulin action remaining at time $t_j$ from said insulin dose, and wherein said future blood glucose value $G(t_j)$ is determined in further dependence upon said insulin action value $F_k(t_j)$.

42. The method of claim 40, wherein the step of determining said future blood glucose value $G(t_j)$ is preceded by the steps of determining in said processor an ultimate time point at which said insulin dose will have no insulin action remaining and setting time $t_j$ equal to said ultimate time point.

43. The method of claim 40, further comprising the steps of determining in said processor a plurality of future blood glucose values representative of a corresponding plurality of expected blood glucose concentrations of the patient and displaying said future blood glucose values in graphical form on said display.

44. The method of claim 40, wherein said corrective action comprises an administration of a supplemental insulin dose, and said method further comprises the steps of storing in said memory a target blood glucose value of the patient and determining in said processor said supplemental insulin dose in dependence upon said insulin sensitivity value and a difference between said future blood glucose value $G(t_j)$ and said target blood glucose value.

45. The method of claim 40, wherein said corrective action comprises a consumption of a number of grams of carbohydrates, and said method further comprises the steps of storing in said memory a target blood glucose value of the patient and determining in said processor said number of grams in dependence upon a difference between said future blood glucose value $G(t_j)$ and said target blood glucose value.

46. The method of claim 40, further comprising the steps of storing in said memory, a hypoglycemic value indicative of a hypoglycemic threshold of the patient, determining in said processor if said future blood glucose value $G(t_j)$ lies below said hypoglycemic value, and audibly alerting the patient when said future blood glucose value $G(t_j)$ lies below said hypoglycemic value.

47. The method of claim 40, wherein said input means comprises a blood glucose meter and the step of entering said blood glucose value $G(t_d)$ comprises the steps of measuring a blood sample of the patient with said glucose meter and producing said blood glucose value $G(t_d)$ from a measurement of said blood sample.

48. The method of claim 40, wherein said insulin dose has an insulin type, said method further comprises the steps of entering said insulin type in said processor, and wherein said insulin action value $F_k(t_d)$ is determined in dependence upon said insulin type.

49. The method of claim 48, wherein said insulin type is selected from the group consisting of regular insulin and lispro insulin.

50. The method of claim 40, further comprising the steps of entering in said processor a plurality of blood glucose values and a plurality of insulin dose values, determining from said glucose values and said insulin dose values an adjusted insulin dose values an adjusted insulin sensitivity value, and storing said adjusted insulin sensitivity value in said memory.

* * * * *